United States Patent [19]
Edwards et al.

[11] Patent Number: 6,087,336
[45] Date of Patent: Jul. 11, 2000

[54] PEPTIDE DERIVATIVES USEFUL IN TREATING AUTOIMMUNE DISEASES

[75] Inventors: Philip Neil Edwards; Richard William Arthur Luke; Ronald Cotton, all of Macclesfield, United Kingdom

[73] Assignee: Zeneca Limited, Macclesfield, United Kingdom

[21] Appl. No.: 09/125,517

[22] PCT Filed: Feb. 18, 1997

[86] PCT No.: PCT/GB97/00438

§ 371 Date: Aug. 20, 1998

§ 102(e) Date: Aug. 20, 1998

[87] PCT Pub. No.: WO97/31023

PCT Pub. Date: Aug. 28, 1997

[30] Foreign Application Priority Data

Feb. 23, 1996 [GB] United Kingdom .................. 9603855
Oct. 5, 1996 [GB] United Kingdom .................. 9620819

[51] Int. Cl.$^7$ .................. A61K 38/08; A61K 38/10; C07K 7/06; C07K 7/08
[52] U.S. Cl. .................. 514/14; 514/15; 514/16; 530/327; 530/328; 530/332
[58] Field of Search .................. 514/14, 15, 16, 514/17; 530/327, 328, 329, 332

[56] References Cited

U.S. PATENT DOCUMENTS

| | | | |
|---|---|---|---|
| 4,474,778 | 10/1984 | Gordon et al. | 546/243 |
| 4,680,283 | 7/1987 | Veber et al. | 514/17 |
| 5,166,136 | 11/1992 | Ward et al. | 514/15 |
| 5,223,485 | 6/1993 | Kawai et al. | 514/16 |
| 5,331,089 | 7/1994 | Curtis et al. | 530/317 |
| 5,719,296 | 2/1998 | Acton, III et al. | 548/550 |

FOREIGN PATENT DOCUMENTS

| | | |
|---|---|---|
| 1413488 | 10/1988 | Australia . |
| 8676291 | 5/1992 | Australia . |
| 284942 | 10/1988 | European Pat. Off. . |
| 0644197 | 3/1995 | European Pat. Off. . |
| 4034829 | 5/1992 | Germany . |
| 9202543 | 2/1992 | WIPO . |
| 9305011 | 3/1993 | WIPO . |
| 9507707 | 3/1995 | WIPO . |
| 9526980 | 10/1995 | WIPO . |
| 9630035 | 10/1996 | WIPO . |
| 9716425 | 5/1997 | WIPO . |
| 9731023 | 8/1997 | WIPO . |

OTHER PUBLICATIONS

Brown et al., Nature, vol. 364, Jul. 1, 1993, pp. 33–39.
Gregory, G.I., *Recent Advances in the Chemistry of β–Lactam Antibiotics*, 1980, pp. 151–169.
Cunningham et al., Bioorg. Med. Chem. Lett., 7(1), 19–24, (1997).
Hanson et al., Bioorg. Med. Chem. Lett., 6(16), 1931–1936 (1996).
Powell et al., J. Pharmaceutical Science, 81(8), 731–5 (1992).
Powell et al., Pharmaceutical Research, 10(9), 1268–73 (1993).
O'Sullivan et al., J. Immunology, 145(6), 1799–1808 (1990).
O'Sullivan et al., J. Immunology, 147(8), 2663–2669 (1991).
O'Sullivan et al., J. Immunology, 146(4), 1240–6 (1991).
Chicz et al., Nature, 358, 764–8 (1992).
Alexander et al., immunity, 1, 751–761 (1994).
Rothbard, et al., Int. Arch. Allergy Immunol., 105, 1–7 (1994).
Hammer et al., J. Exp. Med., 180, 2353–2358 (1994).
Hill et al., J. immunology, 152, 2890–2898 (1994).
Fleckenstein, et al., Eur. J. Biochem., 240, 71–77 (1996).
Hammer et al., Cell, 74, 197–203 (1993).
Hammer et al., Proc. Natl. Acad. Sci. USA, 91, 4456–4460 (1994).
Hammer et al., J. Exp. Med., 176, 1007–1013 (1992).
Hill et al., J. Immunology, 147(1), 189–197 (1991).
Ishioka et al., J. Immunology, 152, 4310–4319 (1994).
Jardetzky et al., The EMBO Journal, 9(6), 1797–1803 (1990).
Jardetzky et al., Proc. Natl. Acad. Sci. USA, 93, 734–738 (1996).
Kropshofer et al., J. Exp. Med., 175, 1799–1803 (1992).
Kropshofer et al., Biochemistry, 30, 9177–9187 (1991).
Rothbard et al., Cold Spring Harbor Symposia on Quantitative Biology, vol. LIV, 431–444 (1989).
Rothbard et al., Int. Immunology, 1(5), 479–86 (1989).
Rotzschke et al., Current Opinion in Immunology, 6, 45–51 (1994).
Sette et al., J. Immunology, 151(6), 3163–70 (1993).
Stern et al., Nature, 368, 215–221 (1994).
Zydowsky et al., J. Org. Chem. 53, 5607–5616 (1988).
Acton et al., Tetrahedron Letters 37(25), 4319–4322 (1996).
Chen et al. CTL Recognition of an Altered Peptide . . . J. Immunol. vol. 157, No. 3, pp. 1000–1005, Aug. 1, 1996.
Ede et al. Identification and Synthesis of Altered Peptides . . . Biomed. Peptides, Proteins & Nucleic Acids. vol. 1, pp. 231–234, 1995.

*Primary Examiner*—Jeffrey E. Russel
*Attorney, Agent, or Firm*—Rothwell, Figg, Ernst & Kurz

[57] ABSTRACT

The invention concerns pharmaceutically useful peptide derivatives of the formula (I): P—$R^1$—$R^2$—$R^3$—$R^4$, in which P, $R^1$, $R^2$, $R^3$, and $R^4$ have the various meanings defined herein, and their pharmaceutically acceptable salts, and pharmaceutical compositions containing them. The novel peptide derivatives are of value in treating MHC class II dependent T-cell mediated autoimmune or inflammatory diseases, such as rheumatoid arthritis. The invention further concerns processes for the manufacture of the novel peptide derivatives and the use of the compounds in medical treatment.

15 Claims, No Drawings

SEQUENCE LISTING (1) GENERAL INFORMATION:

(iii) NUMBER OF SEQUENCES: 62

(2) INFORMATION FOR SEQ ID NO: 1:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:6
            (D) OTHER INFORMATION:/product= "OTHER"
                /note=
                "[(S)-2-((R)-3-amino-2-oxopyrrolidin-1-yl)propanoyl]-
                Ala-piperidine-4-car (xi) SEQUENCE DESCRIPTION: SEQ ID NO: 1:

Xaa Ala Ala Lys Val Xaa
1               5

(2) INFORMATION FOR SEQ ID NO: 2:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:6
            (D) OTHER INFORMATION:/product= "OTHER"
                /note= "[(S)-2-(6-oxo-1,7-diazaspiro[4.4]non-7-yl)
                propanoyl]-Ala-piperidine-4-ca (xi) SEQUENCE DESCRIPTION: SEQ ID NO: 2:

Xaa Ala Ala Lys Val Xaa
1               5

(2) INFORMATION FOR SEQ ID NO: 3:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:4
            (D) OTHER INFORMATION:/product= "OTHER"
                /note= "[(S)-2-((R)-3-amino-2-oxopyrrolidin-1-yl)
                propanoyl]-Ala"

(ix) FEATURE:
            (A) NAME/KEY: Peptide
            (B) LOCATION:6
            (D) OTHER INFORMATION:/product= "OTHER"

```
            /note= "Ala-piperidine-4-carboxamide"

(xi) SEQUENCE DESCRIPTION: SEQ ID NO: 3:

Xaa Lys Ala Xaa Ala Xaa
1               5

(2) INFORMATION FOR SEQ ID NO: 4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Ile"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-4-aminophenylace (xi) SEQUENCE DESCRIPTION: SEQ ID NO: 4:

Xaa Ala Ala Arg Thr Xaa
1               5

(2) INFORMATION FOR SEQ ID NO: 5:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Arg"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-piperidine-4-car (xi) SEQUENCE DESCRIPTION: SEQ ID NO: 5:

Xaa Ala Ala Ala Val Xaa
1               5

(2) INFORMATION FOR SEQ ID NO: 6:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
```

(D) OTHER INFORMATION:/product= "OTHER"
                /note= "5-Phenylpentanoyl-Arg"

(ix) FEATURE:
            (A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-Ala-4-aminophenylace (xi) SEQUENCE DESCRIPTION: SEQ ID NO: 6:

Xaa Ala Ala Ala Thr Xaa
1               5

(2) INFORMATION FOR SEQ ID NO: 7:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-Ala-4-aminophenylace (xi) SEQUENCE DESCRIPTION: SEQ ID NO: 7:

Xaa Ala Ala Arg Val Xaa
1               5

(2) INFORMATION FOR SEQ ID NO: 8:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-Gly-4-aminophenylace (xi) SEQUENCE DESCRIPTION: SEQ ID NO: 8:

Xaa Arg Ala Arg Val Xaa
1               5

(2) INFORMATION FOR SEQ ID NO: 9:

(i) SEQUENCE CHARACTERISTICS:
            (A) LENGTH: 6 amino acids
            (B) TYPE: amino acid

```
                (C) STRANDEDNESS: single
                (D) TOPOLOGY: linear (ii) MOLECULE TYPE: peptide (ix) FEATURE:
                (A) NAME/KEY: Peptide
                (B) LOCATION:1
                (D) OTHER INFORMATION:/product= "OTHER"
                    /note= "5-Phenylpentanoyl-Ala"

(ix) FEATURE:
                (A) NAME/KEY: Peptide
                (B) LOCATION:6
                (D) OTHER INFORMATION:/product= "OTHER"
                    /note= "[(S)-2-((R)-3-amino-2-oxopyrrolidin-1-yl)
                    propanoyl]-Ala-piperidine-4-car (xi) SEQUENCE DESCRIPTION: SEQ ID NO: 9:

Xaa Ile Ala Arg Val Xaa
1               5

(2) INFORMATION FOR SEQ ID NO: 10:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION:1
                (D) OTHER INFORMATION:/product= "OTHER"
                    /note= "5-Phenylpentanoyl-Ala"

(ix) FEATURE:
                (A) NAME/KEY: Peptide
                (B) LOCATION:6
                (D) OTHER INFORMATION:/product= "OTHER"
                    /note= "[(S)-2-((R)-3-amino-2-oxopyrrolidin-1-yl)
                    propanoyl]-Ala-4-aminophenylace (xi) SEQUENCE DESCRIPTION: SEQ ID NO: 10:

Xaa Arg Ala His Val Xaa
1               5

(2) INFORMATION FOR SEQ ID NO: 11:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (ix) FEATURE:
                (A) NAME/KEY: Peptide
                (B) LOCATION:1
                (D) OTHER INFORMATION:/product= "OTHER"
                    /note= "5-Phenylpentanoyl-Ala"

(ix) FEATURE:
                (A) NAME/KEY: Peptide
                (B) LOCATION:6
                (D) OTHER INFORMATION:/product= "OTHER"
                    /note= "[(S)-2-((R)-3-amino-2-oxopyrrolidin-1-yl)
                    propanoyl]-Ala-piperidine-4-car (xi) SEQUENCE DESCRIPTION: SEQ ID NO: 11:

Xaa Ala Asn Arg Val Xaa
```

1               5

(2) INFORMATION FOR SEQ ID NO: 12:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Ala"

(ix) FEATURE:
        (A) NAME/KEY: Peptide
        (B) LOCATION:4
        (D) OTHER INFORMATION:/product= "OTHER"/note=
            "[(S)-2-((R)-3-amino-2-oxopyrrolidin-1-yl)
            propanoyl]-Ala"

(ix) FEATURE:
        (A) NAME/KEY: Peptide
        (B) LOCATION:6
        (D) OTHER INFORMATION:/product= "OTHER"
            /note= "Ala-piperidine-4-carboxamide"

(xi) SEQUENCE DESCRIPTION: SEQ ID NO: 12:

Xaa Arg Ala Xaa Ala Xaa
1               5

(2) INFORMATION FOR SEQ ID NO: 13:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Ala"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Gly-3-aminopropylami (xi) SEQUENCE DESCRIPTION: SEQ ID NO: 13:

Xaa Arg Ala Ala Thr Xaa
1               5

(2) INFORMATION FOR SEQ ID NO: 14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-Gly-3-aminopropylgua"

(xi) SEQUENCE DESCRIPTION: SEQ ID NO: 14:

Xaa Arg Ala Ala Thr Xaa
1               5

(2) INFORMATION FOR SEQ ID NO: 15:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-Gly-NHethyl"

(xi) SEQUENCE DESCRIPTION: SEQ ID NO: 15:

Xaa Arg Ala Arg Thr Xaa
1               5

(2) INFORMATION FOR SEQ ID NO: 16:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-3-guanidinoAla"

(ix) FEATURE:
            (A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-Ala-4-aminophenylace"

(xi) SEQUENCE DESCRIPTION: SEQ ID NO: 16:

Xaa Ala Ala Ala Thr Xaa
1               5

(2) INFORMATION FOR SEQ ID NO: 17:

(i) SEQUENCE CHARACTERISTICS:
            (A) LENGTH: 6 amino acids

```
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1
          (D) OTHER INFORMATION:/product= "OTHER"
              /note= "5-Phenylpentanoyl-3-(tetramethylguanidino)Ala"

(ix) FEATURE:
          (A) NAME/KEY: Peptide
          (B) LOCATION:6
          (D) OTHER INFORMATION:/product= "OTHER"
              /note= "[(S)-2-((R)-3-amino-2-oxopyrrolidin-1-yl)
              propanoyl]-Ala-4-aminophenylace (xi) SEQUENCE DESCRIPTION: SEQ ID NO: 17:

Xaa Ala Ala Ala Thr Xaa
1               5

(2) INFORMATION FOR SEQ ID NO: 18:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1
          (D) OTHER INFORMATION:/product= "OTHER"
              /note= "5-Phenylpentanoyl-Arg"

(ix) FEATURE:
          (A) NAME/KEY: Peptide
          (B) LOCATION:6
          (D) OTHER INFORMATION:/product= "OTHER"
              /note= "[(S)-2-((R)-3-amino-2-oxopyrrolidin-1-yl)
              propanoyl]-Gly-4-(2-aminoethyl)

(xi) SEQUENCE DESCRIPTION: SEQ ID NO: 18:

Xaa Ala Ala Ala Thr Xaa
1               5

(2) INFORMATION FOR SEQ ID NO: 19:

(i) SEQUENCE CHARACTERISTICS:
          (A) LENGTH: 6 amino acids
          (B) TYPE: amino acid
          (C) STRANDEDNESS: single
          (D) TOPOLOGY: linear (ii) MOLECULE TYPE: peptide (ix) FEATURE:
          (A) NAME/KEY: Peptide
          (B) LOCATION:1
          (D) OTHER INFORMATION:/product= "OTHER"
              /note= "5-Phenylpentanoyl-Arg"

(ix) FEATURE:
          (A) NAME/KEY: Peptide
          (B) LOCATION:6
          (D) OTHER INFORMATION:/product= "OTHER"
              /note= "[(S)-2-((R)-3-amino-2-oxopyrrolidin-1-yl)
              propanoyl]-Gly-piperazin-4-yl.C (xi) SEQUENCE DESCRIPTION: SEQ ID NO: 19:
```

```
Xaa Ala Ala Ala Thr Xaa
1               5

(2) INFORMATION FOR SEQ ID NO: 20:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Arg"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Gly-4-aminophenethyl (xi) SEQUENCE DESCRIPTION: SEQ ID NO: 20:

Xaa Ala Ala Ala Thr Xaa
1               5

(2) INFORMATION FOR SEQ ID NO: 21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Ala"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-4-aminophenylace (xi) SEQUENCE DESCRIPTION: SEQ ID NO: 21:

Xaa Ala Ala Arg Thr Xaa
1               5

(2) INFORMATION FOR SEQ ID NO: 22:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Ala"

(ix) FEATURE:
```

(A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-[NH-NH-CO]-4-aminoph (xi) SEQUENCE DESCRIPTION: SEQ ID NO: 22:

Xaa Arg Ala Arg Thr Xaa
1               5

(2) INFORMATION FOR SEQ ID NO: 23:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Ala"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-NH-NH-CONH2"

(xi) SEQUENCE DESCRIPTION: SEQ ID NO: 23:

Xaa Arg Ala Arg Thr Xaa
1               5

(2) INFORMATION FOR SEQ ID NO: 24:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Ala"

(ix) FEATURE:
        (A) NAME/KEY: Peptide
        (B) LOCATION:4
        (D) OTHER INFORMATION:/product= "OTHER"
            /note= "[(S)-2-((R)-3-amino-2-oxopyrrolidin-1-yl)
            propanoyl]-Ala"

(ix) FEATURE:
        (A) NAME/KEY: Peptide
        (B) LOCATION:6
        (D) OTHER INFORMATION:/product= "OTHER"
            /note= "Ala-4-aminophenylacetamide"

(xi) SEQUENCE DESCRIPTION: SEQ ID NO: 24:

Xaa Arg Ala Xaa Arg Xaa
1               5

(2) INFORMATION FOR SEQ ID NO: 25:

(i) SEQUENCE CHARACTERISTICS:

(A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "3-(2-cyanobenzo[b]thiophen-5-yl)propanoyl-Ala"

(ix) FEATURE:
            (A) NAME/KEY: Peptide
            (B) LOCATION:4
            (D) OTHER INFORMATION:/product= "OTHER"
                /note= "[(S)-2-((R)-3-amino-2-oxopyrrolidin-1-yl)
                propanoyl]-Ala"

(ix) FEATURE:
            (A) NAME/KEY: Peptide
            (B) LOCATION:6
            (D) OTHER INFORMATION:/product= "OTHER"
                /note= "Ala-4-aminophenylacetamide"

(xi) SEQUENCE DESCRIPTION: SEQ ID NO: 25:

Xaa Arg Ala Xaa Arg Xaa
1               5

(2) INFORMATION FOR SEQ ID NO: 26:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Arg"

(ix) FEATURE:
            (A) NAME/KEY: Peptide
            (B) LOCATION:4
            (D) OTHER INFORMATION:/product= "OTHER"
                /note= "[(S)-2-((R)-3-amino-2-oxopyrrolidin-1-yl)
                propanoyl]-Ala"

(ix) FEATURE:
            (A) NAME/KEY: Peptide
            (B) LOCATION:6
            (D) OTHER INFORMATION:/product= "OTHER"
                /note= "Ala-4-aminophenylacetamide"

(xi) SEQUENCE DESCRIPTION: SEQ ID NO: 26:

Xaa Ala Ala Xaa Arg Xaa
1               5

(2) INFORMATION FOR SEQ ID NO: 27:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide

```
            (B) LOCATION:1
            (D) OTHER INFORMATION:/product= "OTHER"
                /note= "5-Phenylpentanoyl-Arg"

(ix) FEATURE:
            (A) NAME/KEY: Peptide
            (B) LOCATION:4
            (D) OTHER INFORMATION:/product= "OTHER"
                /note= "[(S)-2-((R)-3-amino-2-oxopyrrolidin-1-yl)
                propanoyl]-Ala"

(ix) FEATURE:
            (A) NAME/KEY: Peptide
            (B) LOCATION:6
            (D) OTHER INFORMATION:/product= "OTHER"
                /note= "Ala-4-aminophenylacetamide"

(xi) SEQUENCE DESCRIPTION: SEQ ID NO: 27:

Xaa Ile Ala Xaa Arg Xaa
1               5

(2) INFORMATION FOR SEQ ID NO: 28:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ile"

(ix) FEATURE:
            (A) NAME/KEY: Peptide
            (B) LOCATION:4
            (D) OTHER INFORMATION:/product= "OTHER"
                /note= "[(S)-2-((R)-3-amino-2-oxopyrrolidin-1-yl)
                propanoyl]-Leu"

(ix) FEATURE:
            (A) NAME/KEY: Peptide
            (B) LOCATION:6
            (D) OTHER INFORMATION:/product= "OTHER"
                /note= "Ala-4-aminophenylacetamide"

(xi) SEQUENCE DESCRIPTION: SEQ ID NO: 28:

Xaa Arg Ala Xaa Arg Xaa
1               5

(2) INFORMATION FOR SEQ ID NO: 29:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Ala"

(ix) FEATURE:
            (A) NAME/KEY: Peptide
            (B) LOCATION:4
            (D) OTHER INFORMATION:/product= "OTHER"
                /note= "[((R)-3-amino-2-oxopyrrolidin-1-yl)acetyl]-Ala"
```

(ix) FEATURE:
            (A) NAME/KEY: Peptide
            (B) LOCATION:6
            (D) OTHER INFORMATION:/product= "OTHER"
                /note= "Ala-4-aminophenylacetamide"

(xi) SEQUENCE DESCRIPTION: SEQ ID NO: 29:

Xaa Arg Ala Xaa Ala Xaa
1               5

(2) INFORMATION FOR SEQ ID NO: 30:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-Arg"

(ix) FEATURE:
            (A) NAME/KEY: Peptide
            (B) LOCATION:4
            (D) OTHER INFORMATION:/product= "OTHER"
                /note= "[(S)-2-((R)-3-amino-2-oxopyrrolidin-1-yl)
                propanoyl]-Ala"

(ix) FEATURE:
            (A) NAME/KEY: Peptide
            (B) LOCATION:6
            (D) OTHER INFORMATION:/product= "OTHER"
                /note= "Ala-4-aminophenylacetamide"

(xi) SEQUENCE DESCRIPTION: SEQ ID NO: 30:

Xaa Ala Ala Xaa Ala Xaa
1               5

(2) INFORMATION FOR SEQ ID NO: 31:

(i) SEQUENCE CHARACTERISTICS:
            (A) LENGTH: 6 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "5-Phenylpentanoyl-tetramethylhomoArg-"

(ix) FEATURE:
            (A) NAME/KEY: Peptide
            (B) LOCATION:6
            (D) OTHER INFORMATION:/product= "OTHER"
                /note= "[(S)-2-((R)-3-amino-2-oxopyrrolidin-1-yl)
                propanoyl]-Ala-4-aminophenylace (xi) SEQUENCE DESCRIPTION: SEQ ID NO: 31:

Xaa Ala Ala Ala Thr Xaa
1               5

(2) INFORMATION FOR SEQ ID NO: 32:

```
    (i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Arg"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-(4-aminophenyl.C (xi) SEQUENCE DESCRIPTION: SEQ ID NO: 32:

Xaa Ala Ala Ala Thr Xaa
1               5

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Arg"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-4-aminophenylace methyl ester"

(xi) SEQUENCE DESCRIPTION: SEQ ID NO: 33:

Xaa Ala Ala Ala Thr Xaa
1               5

(2) INFORMATION FOR SEQ ID NO: 34:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Arg"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-4-aminophenyl ac
```

(xi) SEQUENCE DESCRIPTION: SEQ ID NO: 34:

Xaa Ala Ala Ala Thr Xaa
1               5

(2) INFORMATION FOR SEQ ID NO: 35:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Arg"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-4-aminophenylace (xi) SEQUENCE DESCRIPTION: SEQ ID NO: 35:

Xaa Ala Ala Ala Thr Xaa
1               5

(2) INFORMATION FOR SEQ ID NO: 36:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Dpr"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-4-aminophenylace (xi) SEQUENCE DESCRIPTION: SEQ ID NO: 36:

Xaa Ala Ala Ala Thr Xaa
1               5

(2) INFORMATION FOR SEQ ID NO: 37:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

Ala Ala Ala Lys Val
1               5

(2) INFORMATION FOR SEQ ID NO: 38:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

Ala Lys Ala Ala Val
1               5

(2) INFORMATION FOR SEQ ID NO: 39:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

Ala Ala Ala Arg Val
1               5

(2) INFORMATION FOR SEQ ID NO: 40:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

Ala Arg Ala Ala Val
1               5

(2) INFORMATION FOR SEQ ID NO: 41:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 41:

Ala Lys Ala Lys Val
1               5

(2) INFORMATION FOR SEQ ID NO: 42:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 42:

Ala Arg Ala Arg Val
1               5

(2) INFORMATION FOR SEQ ID NO: 43:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 43:

Ala Arg Ala Lys Val
1          5

(2) INFORMATION FOR SEQ ID NO: 44:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 44:

Ala Lys Ala Arg Val
1          5

(2) INFORMATION FOR SEQ ID NO: 45:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 45:

Ile Ala Ala Arg Thr
1          5

(2) INFORMATION FOR SEQ ID NO: 46:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 46:

Arg Ala Ala Ala Val
1          5

(2) INFORMATION FOR SEQ ID NO: 47:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Arg Ala Ala Ala Thr 1               5

(2) INFORMATION FOR SEQ ID NO: 48:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Ala Ala Ala Arg Thr
1               5

(2) INFORMATION FOR SEQ ID NO: 49:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Ala Arg Ala Arg Thr
1               5

(2) INFORMATION FOR SEQ ID NO: 50:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Ala Ile Ala Arg Val
1               5

(2) INFORMATION FOR SEQ ID NO: 51:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Ala Arg Ala His Val
1               5

(2) INFORMATION FOR SEQ ID NO: 52:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

```
Ala Arg Ala Ala Thr
1               5

(2) INFORMATION FOR SEQ ID NO: 53:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

Ala Ala Asn Arg Val
1               5

(2) INFORMATION FOR SEQ ID NO: 54:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "3-guanidinoAla"

(xi) SEQUENCE DESCRIPTION: SEQ ID NO: 54:

Xaa Ala Ala Ala Thr
1               5

(2) INFORMATION FOR SEQ ID NO: 55:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "3-(tetramethylguanidino)Ala"

(xi) SEQUENCE DESCRIPTION: SEQ ID NO: 55:

Xaa Ala Ala Ala Thr
1               5

(2) INFORMATION FOR SEQ ID NO: 56:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:4
        (D) OTHER INFORMATION:/product= "OTHER"
            /note= "cyclohexylAla"
```

(xi) SEQUENCE DESCRIPTION: SEQ ID NO: 56:

Tyr Ala Ala Xaa
1

(2) INFORMATION FOR SEQ ID NO: 57:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 57:

Tyr Ala Ala Phe
1

(2) INFORMATION FOR SEQ ID NO: 58:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 58:

Ala Phe Phe Phe
1

(2) INFORMATION FOR SEQ ID NO: 59:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 59:

Ala Ala Ala Phe
1

(2) INFORMATION FOR SEQ ID NO: 60:

(i) SEQUENCE CHARACTERISTICS:
            (A) LENGTH: 15 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION:1
            (D) OTHER INFORMATION:/product= "OTHER"
                /note= "biotinyl-2-aminohexanoyl"

(xi) SEQUENCE DESCRIPTION: SEQ ID NO: 60:

Xaa Pro Lys Tyr Val Lys Gln Asn Thr Leu Lys Leu Ala Thr Gly
1               5                   10                  15

(2) INFORMATION FOR SEQ ID NO: 61:

```
(i) SEQUENCE CHARACTERISTICS:
    (A) LENGTH: 14 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 61:

Pro Lys Tyr Val Lys Gln Asn Thr Leu Lys Leu Ala Thr Gly
1               5                  10

(2) INFORMATION FOR SEQ ID NO: 62:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION:1
        (D) OTHER INFORMATION:/product= "OTHER"
            /note= "5-Phenylpentanoyl-Lys-"

(ix) FEATURE:
        (A) NAME/KEY: Peptide
        (B) LOCATION:6
        (D) OTHER INFORMATION:/product= "OTHER"
            /note= "[(S)-2-((R)-3-amino-2-oxopyrrolidin-1-yl)
            propanoyl]-Ala-4-aminophenylace (xi) SEQUENCE DESCRIPTION: SEQ ID NO: 62:

Xaa Ala Ala Ala Thr Xaa
1               5
```

PEPTIDE DERIVATIVES USEFUL IN TREATING AUTOIMMUNE DISEASES

The present invention relates to certain novel peptide derivatives which possess pharmacologically useful properties for use in treating autoimmune diseases or medical conditions, such as rheumatoid arthritis and other MHC class II dependent T-cell mediated diseases. The invention also includes pharmaceutical compositions of the novel chemical compounds, processes for their manufacture, and their use in treating one or more of the aforementioned diseases or medical conditions and in the production of novel pharmaceuticals for use in such medical treatments.

Stimulation of the human immune response is dependent on the recognition of protein antigens by T cells. However T cells cannot respond to antigen alone and are only triggered by antigen when it is complexed with major histocompatibility complex (MHC) molecules on the surface of an antigen presenting cell, such as a B cell, macrophage or dendritic cell.

MHC class I molecules elicit a T-killer cell response which results in the destruction of the cell bearing the antigen. MHC class II molecules elicit a T-helper cell response which controls the expansion and maturation of selected B cells (i.e. generation of antigen-specific antibodies) and activation of macrophages.

A critical requirement of the immune system is the ability to differentiate between "self" and "non-self" (i.e. foreign) antigens. This discrimination is required to enable the immune system to mount a response to invading foreign pathogens whilst maintaining tolerance to self-proteins and thereby preventing damage to normal tissues. An autoimmune disease results when self-tolerance breaks down allowing the immune system to react against self-tissues such as the joints in rheumatoid arthritis. It is thought that the maintenance of tolerance and thus avoidance of autoimmune disease is critically dependent on the function of MHC molecules.

The observation that many autoimmune diseases are linked to the inheritance of particular MHC alleles suggests a key role for MHC molecules in the pathogenesis of autoimmune disease. For instance multiple sclerosis is linked to the inheritance of HLA-DR2, insulin dependent diabetes mellitus to HLA-DR3 and/or HLA-DR4 and Hashimoto's thyroiditis to HLA-DR5. In particular, an especially strong association exists between predisposition to development of the chronic inflammatory joint disease rheumatoid arthritis and the inheritance of HLA-DR4Dw4 and/or HLA-DR4w14 and/or HLA-DR1. It is thought that the autoimmune disease associated MHC molecules bind to certain self-antigens and present them to T cells thus stimulating an autoimmune response. Other peptides which can bind to the autoimmune associated MHC molecules and/or either prevent the binding or displace already bound self-antigens and/or which inhibit T cell activation (especially the activity of pathogenic T cells (e.g. Th 1 cells)) and/or which increase the activity of protective T cells (e.g. Th 2 cells), or peptides which interact with MHC molecules by an alternative mechanism of action so as to prevent or modify stimulation of an autoimmune response mediated via said MHC molecules, may specifically suppress an autoimnmune response.

An agent of this kind would offer therapy for the autoimmune disease whilst avoiding general suppression of the immune system, thus limiting deleterious side-effects. This kind of profile would have significant advantages over current therapy for diseases such as rheumatoid arthritis. It is contemporary practice to treat rheumatoid arthritis initially with symptom relief agents such as NSAIDs, which do not have any beneficial effect on disease progression and are often associated with unwanted side-effects. Treatment of more severe disease relies on the use of the so-called second-line agents. Often these are general cytotoxic compounds which are of limited efficacy and can cause severe toxicity problems. A rationally based, disease modifying agent, without associated non-specific cytotoxicity, would therefore offer significant benefits in the treatment of rheumatoid arthritis.

Peptides are disclosed in International Patent Application, Publication Nos. WO 92/02543, WO 93/05011 and WO 95/07707 which bind MHC molecules and inhibit T-cell activation.

Although a number of peptides have been discovered which inhibit HLA-DR restricted T cell activation by binding to HLA-DR molecules, there is a continuing need for alternative compounds which bind to such molecules and/or either prevent the binding or displace already bound self antigens and/or inhibit T-cell activation and/or increase the activity of protective T-cells, or which interact with MHC molecules by an alternative mechanism of action, so as to prevent or modify stimulation of an autoimmune response that causes a disease or condition referred to above.

We have discovered that the peptide derivatives of the present invention (set out below) surprisingly possess such pharmacologically useful properties and this is a basis for the present invention.

According to one aspect of the invention there is provided a peptide derivative of the formula I (set out hereinafter)
wherein
P is a hydrophobic residue; $R^1$ is a sequence of 5 L-amino acids and $R^3$ is a single L-amino acid; or $R^1$ is a sequence of 3 L-amino acids and $R^3$ is a sequence of 3 L-amino acids; $R^2$ is a group of the formula II (set out hereinafter) or III (set out hereinafter) in which Ra and Rb are independently selected from hydrogen and (1–4C)alkyl and A is methylene ($CH_2$) or oxygen; and
$R^4$ is OH, $NH_2$ or NRcRd wherein Rc is selected from (1–4C)alkyl, 2-carbamoylcyclopentyl, 2-pyridylmethyl, 4-carbamoylcyclohexyl, 4-carbamoylcyclohexylmethyl, 3-carbamoylphenyl, 4-carbamoylphenyl, 4-(carbamoyhnethyl)phenyl, 4-(carboxymethyl)phenyl, 4-(methoxycarbonylmethyl) phenyl, 2-morpholinoethyl and a group of the formula $-A^1-G^1$ in which $A^1$ is (3–7C)alkylene or
AHU 1is selected from
(1) a group of the formula $-A^2-B^2-$ in which $A^2$ is p-phenylene or 1.4-cyclohexylene and $B^2$ is (1–4C)alkylene or $A^2$ is methylene and $B^2$ is p-phenylene or 1,4-cvclohexylene; and
(2) a group of the formnula $-A^3-B^3-C^3-$ in which $A^3$ is methylene, $B^3$ is p-phenylene or 1.4-cyclohexylene and $C^3$ is (1–3C)alkylene; and
$G^1$ is a group of the formula $—N=C[N(Rp)_2]_2$ in which each Rp is independently selected from hydrogen, methyl, ethyl and propyl;
or $A^1$ is a group of the formula $-A^4-B^4-$ in which $A^4$ is p-phenylene and $B^4$ is $—CH_2—CO—$ and
$G^1$ is 2-morpholinoethyl or 4-[2-(2-hydroxyethoxy)ethyl] piperazin-1-yl;
and Rd is hydrogen or (1–4C)alkyl; or
$R^4$ is 1-piperazinyl, 4-methyl-1-piperazinyl, 4-amidino-1-piperazinyl, 4-(2-(2-hydroxyethoxy)ethyl)-1-piperazinyl, 1-piperidyl or 4-substituted-1-piperidyl wherein the 4-substitutent is selected from carboxy, carbamoyl, N-(2-aminoethyl)carbamoyl and N-(4-aminobutyl)carbamoyl; or $R^4$ is a sequence of 1 to 6 amino acids or an amide thereof; or a pharmaceutically acceptable salt thereof.

It is to be understood that an amino acid of $R^4$ may independently have the D- or L-stereochemistry.

Furthermore, when R4 is defined as hydroxy (OH), this will be understood to be the hydroxy group of the C-terminal amino acid of $R^3$. Similarly where $R^4$ is defined as $NH_2$. NRcRd, piperazinyl, piperidyl; etc., this means that the hydroxy group of the C-terminal amino acid of $R^3$ is replaced by such a group. It is also to be understood that where an amino acid is referred to this means an alpha-amino acid. It is also to be understood that when an L-amino acid is referred to this also includes amino acids such as Gly, 2,2-diethylGly, aza-alanine and aza-glycine which have no chiral carbon atom. It is farther to be understood that generic terms such as "alkyl" include both straight and branched chain variants when the carbon numbers permit. The same convention applies to other radicals.

It is well known in the art that compounds having a chiral centre may exist in the form of a racemate (or a mixture of diastereoisomers where there is more than one chiral centre) or as an optically active enantiomer or diastereoisomer. It is also well known in the art that a particular biological activity associated with a racemic or diastereomeric mixture may result largely or solely from a single optically active isomer. It will therefore be understood that the invention concerns any form of a peptide derivative of formula I which possesses the aforementioned pharmaceutically useful properties. It is well known in the art how to obtain a single optically active isomer, for example by separation from a racemic or diastereomeric mixture containing the isomer using conventional techniques such as chromatography, or by chiral synthesis using an appropriate optically active starting material or intermediate, as exemplified herein. It is also well known in the art how to determine the pharmacological properties of such racemic or diastereomeric mixtures, and the individual optically active isomers, for example by using the assays described herein. The person skilled in the art is therefore easily able to obtain the particular isomers of the peptide derivatives of formula I having the beneficial pharmacological properties referred to herein.

It is also to be understood that the present invention also encompasses any polymorphic form, any tautomer or any solvate, or any mixture thereof of a peptide derivative of formula I which possesses the beneficial pharmacological properties referred to herein.

Suitable independent values for the α-amino acids comprising $R^1$ and $R^3$ include, for example, the 20 naturally occurring amino acids encoded by the genetic code, particularly alanine (Ala), glutamic acid (Glu), glycine (Gly), histidine (His), isoleucine (Ile), lysine (Lys), asparagine (Asn), glutamine (Gln), arginine (Arg), threonine (Thr), valine (Val) and proline (Pro). Amino acids such as sarcosine (Sar), 3,3,3, trifluoroalanine. 2.2-diethylglycine, 2,3-diaminopropanoic acid (Dap), 2,4-diaminobutanoic acid (Dab), 2-aminobutanoic acid (Abu), homoarginine, homophenylalanine, trans4-hydroxyproline (Hyp) aza-alanine [$H_2N$—$N(CH_3)$—COOH; Azala], aza-glycine [$H_2N$—NH—COOH: Azgly]. 1.2.3.4-tetrahydroisoquinoline-3-carboxylic acid (Tic), octahydroindole-2-carboxylic acid (Oic), decahydroisoquinoline-3- carboxylic acid (Dic) are also suitable. (Where Dic is referred to this means the forms in which the ring-junctions both have the R configuration or both have the S configuration.) Corresponding $N^2$-methylated amino acids may also be used, as well as corresponding amino acids in which a free side-chain carboxylic acid function is esterified (for example as an (1–6C) alkyl or benzyl ester) and a free side-chain amino group is alkylated (for example, methylated), acetylated or converted to a carbamate (for example, an alkyl (such as methyl or ethyl), phenyl or benzyl carbamate). Other suitable values for $R^1$ and $R^3$ include, for example, 2-substituted glycine in which the 2-substituent is a group of the formula —($CH_2$)$_s$$NH_2$ wherein s is 1 to 3, or a group of the formula —($CH_2$)$_p$N(Re)$_3^+$.X$^-$wherein p is 2 to 4 and X$^-$ is a counter ion (such as acetate, trifluoroacetate, hydroxide or chloride), or a group of the formula —($CH_2$)$_q$N(Re)$_2$ wherein q is 0 to 4 or a group of the formula —($CH_2$),N=C[N(Re)$_2$]$_2$ wherein r is 1 to 4, wherein in which last three groups each Re is independently selected from hydrogen and (1–4C) alkyl (such as methyl or ethyl).

A value for $R^1$ of particular interest when it is a sequence of 5 amino acids includes, for example, a sequence in which the fifth amino acid (as read from left to right) is Val or Thr and a sequence in which the fourth and fifth amino acids is Lys-Val, Arg-Val, Lys-Thr, Arg-Thr, Ala-Val or Ala-Thr.

A particular value for $R^1$ when it is a sequence of 5 amino acids includes, for example, Ala-Ala-Ala-Lys-Val (SEQ ID NO:37), Ala-Lys-Ala-Ala-Val (SEQ ID NO:38), Ala-Ala-Ala-Arg-Val (SEQ ID NO:39), Ala-Arg-Ala-Ala-Val (SEQ ID NO:40), Ala-Lys-Ala-Lys-Val (SEQ ID NO:41), Ala-Arg-Ala-Arg-Val (SEQ ID NO:42), Ala-Arg-Ala-Lys-Val (SEQ ID NO:43), Ala-Lys-Ala-Arg-Val (SEQ ID NO:44), Ile-Ala-Ala-Arg-Thr (SEQ ID NO:45), Arg-Ala-Ala-Ala-Val (SEQ ID NO:46), Arg-Ala-Ala-Ala-Thr (SEQ ID NO:47), Ala-Ala-Ala-Arg-Thr (SEQ ID NO:48), Ala-Arg-Ala-Arg-Thr (SEQ ID NO:49), Ala-Ile-Ala-Arg-Val (SEQ ID NO:50), Ala-Arg-Ala-His-Val (SEQ ID NO:51), Ala-Arg-Ala-Ala-Thr (SEQ ID NO:52), Ala-Ala-Asn-Arg-Val (SEQ ID NO:53) or X-Ala-Ala-Ala-Thr where X is —NH.CH[$CH_2$NH.C(=NH).$NH_2$].CO— (hereinafter referred to as "Gap (SEQ ID NO:54)"), or —NH.CH($CH_2$N=C[N($CH_3$)$_2$]$_2$).CO— (hereinafter referred to as "GapMe$_4$(SEQ ID NO:55)"), of which Ala-Ala-Ala-Lys-Val (SEQ ID NO:37), Arg-Ala-Ala-Ala-Val (SEQ ID NO:46), Arg-Ala-Ala-Ala-Thr (SEQ ID NO:47), Ala-Ala-Ala-Arg-Thr (SEQ ID NO:48), Ala-Arg-Ala-Arg-Thr (SEQ ID NO:49), Gap-Ala-Ala-Ala-Thr (SEQ ID NO:54) and GapMe$_4$-Ala-Ala-Ala-Thr (SEQ ID NO:50) are preferred. Arg-Ala-Ala-Ala-Val (SEQ ID NO:46) and Arg-Ala-Ala-Ala-Thr (SEQ ID NO:47) are particularly preferred.

A value for $R^1$ of particular interest when it is a sequence of 3 amino acids includes, for example, a sequence in which the amino acid adjacent to $R^2$ is Ala and a sequence in which the second and third amino acids (as read from left to right) is Lys-Ala, Arg-Ala, Ile-Ala and Ala-Ala.

A value for $R^1$ of special interest when it is a sequence of three amino acids includes, for example, Ala-Lys-Ala, Ala-Arg-Ala, Arg-Ala-Ala, Arg-lle-Ala and Ile-Arg-Ala, especially Ala-Arg-Ala.

A value for $R^3$ of particular interest when it is a sequence of three amino acids includes, for example, a sequence in which the first amino acid (as read from left to right, i.e. adjacent to $R^2$) is Ala or Leu.

A preferred value for $R^3$ when it is a sequence of three amino acids includes, for example, Ala-Ala-Ala, Leu-Arg-Ala and especially Ala-Arg-Ala.

A preferred value for $R^3$ when it is a single amino acid includes, for example, Ala, Gly and Azgly, especially Ala.

Particular values for Ra and Rb when they are alkyl include, for example, methyl, ethyl and propyl.

A preferred value for Ra and Rb includes, for example, hydrogen and methyl.

A suitable value for the hydrophobic residue P (which it will be appreciated is attached to the amino group of the N-terminal amino acid of $R^1$) includes, for example, an organic hydrophobic group such as a hydrophobic aliphatic aromatic, heteroaromatic or mixed aliphatic/aromatic or aliphatic/heteroaromatic organic group of from 5 to 20 carbon atoms (and 1, 2 or 3 heteroatoms selected from oxygen, sulphur and nitrogen for heteroaryl-containing groups), for example a group of the formula R—, R.CO—. R.$SO_2$—, R.O.CO—, R.NHCO—, R.O.CS—, R.S.CO—, R.NHCS—, R.S.CS— and R.CS—, in which R includes, for example, (5–10C)alkyl, aryl, heteroaryl, aryl(2–10C)alkyl, heteroaryl(2–10C)alkyl, diaryl(2–8C)alkyl, aryl(2–10C) alkenyl, arylcyclopropyl, (5–10C)cycloalkyl, (5–10C) cycloalkyl(2–6C)alkyl, 3-biphenyl, 4-biphenyl, 4-cyclohexylphenyl, 2-naphthyloxymethyl, 3-naphthyloxymethyl, phenoxyphenyl and tetrahydronaphthyl, an aryl or heteroaryl group of which values of R may bear one or more (1–4C)alkyl, halogeno, cyano or (1–4C)alkoxy substituents. One particular embodiment of the invention includes, for example, peptide derivatives of the formula I in which P is R.CO— as defined above. A further particular embodiment of the invention includes, for example, peptide derivatives of the formula I wherein P is a hydrophobic aliphatic, aromatic or aliphatic/aromatic organic group of from 5 to 20 carbon atoms.

Particular values for R include, for example, when it is (5–10C)alkyl: pentyl, isopentyl, tert-pentyl, 2-methylpentyl, hexyl, isohexyl, 5-methylhexyl and octyl; when it is aryl: phenyl, naphthyl and indenyl; when it is heteroaryl: 2-, 3-, 5- or 6-indolyl, 2-, 3-, 5- or 6-indolinyl 2-, 3-, 5- or 6-benzo[b]thiophenyl, thienyl, 2-, 4- or 5-benzothiazolyl, 2-, 4- or 5-benzoxazolyl, 2-, 4- or 5-benzimidazolyl, 1,4-benzodioxanyl attached at the 2-, 3-, 6- or 7-position and 2-, 3-, 5- or 6-benzofliranyl; when it is aryl(2–10C)alkyl: aryl (2–6C)alkyl (where the aryl portion includes, for example, any of the specific values for aryl given above and the (2–6C)alkyl portion includes, for example, methylene, ethylene, trimethylene, tetramethylene and pentamethylene) such as 2-phenylethyl, 3-phenylpropyl, 4-phenylbutyl and 5-phenylpentyl; when it is heteroaryl(2–10C)alkyl: heteroaryl(2–6C)alkyl (where the heteroaryl portion includes, for example, any of the specific values for heteroaryl given above and the (2–6C)alkyl portion includes, for example, methylene, ethylene, trimethylene, tetramethylene and pentamethylene) such as in 2-(2-cyanobenzo[b] thiophen-5-yl)ethyl; when it is diaryl(2–8C)alkyl: diaryl (2–6C)alkyl such as 2,2-diphenylethyl, 3,3-diphenylpropyl and 4,4-diphenylbutyl; when it is aryl(2–10C)alkenyl: aryl (2–6C)alkenyl such as styryl, 3-phenylpropen-2-yl and 4-phenylbuten-1-yl; when it is arylcyclopropyl: phenylcyclopropyl, 1-naphthylcyclopropyl and 2-naphthyicyclopropyl; when it is (5–10C)cycloalkyl: cyclopentyl, cyclohexyl and 1-adamantyl; and when it is (5–10C)cycloalkyl(2–6C)alkyl: 2-(cyclohexyl)ethyl, 3-(cyclohexyl)propyl and 4-(cyclohexyl)butyl. A particular value for a substituent on an aryl group of R includes, for example, methyl, ethyl, chloro, bromo, iodo, methoxy, ethoxy and cyano.

The hydrophobic residue P also includes, for example, a hydrophobic L-amino acid, such as phenylalanine (Phe) and hydrogenated analogues thereof such as cyclohexylalanine (Cha), para-chloroPhe, 3-(2-thienyl)alanine, tyrosine (Tyr), Tyr(Omethyl), tryptophan (Trp), biphenylalanine, 3-(1-naphthyl)alanine, 3-(2-naphthyl)alanine and hydrogenated analogues thereof, 3-(1-adamantyl)alanine (Ada), Glu (OBenzyl), 3-(benzyloxy)Ala, 3-(benzylsulfanyl)Ala and 9-fluorenylGly, each of which may optionally bear on the N-terminus a hydrophobic aliphatic, aromatic, heteroaromatic or mixed aliphatic/aromatic or aliphatic/ heteroaromatic organic group as defined or exemplified above. Alternatively, the hydrophobic amino acid may optionally bear, for example, a further sequence of 1 to 3 amino acids selected from any of the values for $R^1$ and $R^3$ defined above. For example P includes the particular sequences Ala-Cha, Ala-Ala-Cha, Tyr-Ala-Ala-Cha (SEQ ID NO:56), Tyr-Ala-Ala-Phe (SEQ ID NO:57), Ala-Phe-Phe-Phe (SEQ ID NO:58) and Ala-Ala-Ala-Phe (SEQ ID NO:59). The first amino acid of such further sequence of 1 to 3 amino acids (as read from left to right) may be an L- or D-amino acid and may also optionally bear a hydrophobic aliphatic, aromatic, heteroaromatic or mixed aliphatic/ aromatic or aliphatic/heteroaromatic organic group as defined or exemplified above.

Further particular values for P include, for example, 3-(benzyloxycarbonyl)propionyl-Phe, 3-(benzyloxycarbonyl)propionyl-Cha, 4-(benzyloxycarbonyl)butyryl-Phe, 4-(benzyloxycarbonyl) butyryl-Cha, (5-oxo-pyrrolidin-2-yl)carbonyl-Phe-Tyr, (5-oxo-pyrrolidin-2-yl)carbonyl-Glu(OBenzyl)-Tyr, acetyl-Glu(OBenzyl)-Tyr, diphenylmethyl.CONH.CH$_2$CH$_2$.CO-Cha, diphenylmethyl.CONH.CH$_2$CH$_2$.CO-Tyr, diphenylmethyl.CONH.CH$_2$CH$_2$CH$_2$.CO-Cha, diphenylmethyl.CONH.CH$_2$CH$_2$CH$_2$.CO-Tyr, diphenylmethyl.NHCO.CH$_2$CH$_2$CH$_2$.CO-Cha, diphenylmethyl.NHCO.CH$_2$CH$_2$CH$_2$.CO-Tyr, benzyl.NHCO.CH$_2$CH$_2$.CO-Cha, benzyl.NHCO.CH$_2$CH$_2$.CO-Tyr. N-acetyl-4-chloro-beta-hydroxyPhe, 4-phenoxyphenyl .NHCO—, benzyl.NHCO.CH$_2$CH$_2$.CO .(N-methylPhe), benzyl.NHCO.CH$_2$CH$_2$.CONH.CH(CHPh$_2$).CO, benzyl.NHCO.CH$_2$CH$_2$.CO-Tyr, 3,3-diphenyipropionyl, trans-cinnamoyl, 5-phenyivaleryl and 3-(2-cyanobenzo[b] thiophen-5-yl)propionyl.

A value for P of particular interest includes, for example, Ph.(CH$_2$)$_4$.CO-(5-phenylvaleryl (Phv)), Ph.(CH$_2$)$_4$.CS- and 3-(2-cyanobenzo[b]thiophen-5-yl)propionyl.

A preferred value for the hydrophobic residue P includes, for example, 3-(2-cyanobenzo[b]thiophen-5-yl)propionyl and 5-phenylvaleryl (Phv), especially the latter.

When Rc is a group of the formula -A$^1$-G$^1$, a particular value for A$^1$ when it is alkylene includes, for example, methylene, ethylene, propylene and butylene; a particular value for B$^2$ when is is (1–4C)alkylene includes, for example, methylene, ethylene and propylene; and a particular value for C$^3$ when it is (1–3C)alkylene includes, for example, methylene, ethylene and propylene.

A particular value for -A$^1$-G$^1$ includes, for example, 3-guanidinopropyl, 4-(2-guanidinoethyl)phenyl, 4-(2-morpholinoethyl.NH.CO.CH$_2$)phenyl and 4-(4-[2-(2-hydroxyethoxy)ethyl]piperazin-1-yl.CO.CH$_2$)phenyl.

A particular value for R$^4$ when it is a sequence of 1 to 6 amino acids or an amide thereof, includes, for example a sequence of L-amino acids independently selected from any of the values for R$^1$ and R$^3$ defined above (such as Ala-Thr-Gly-OH), or their D-analogues, or a sequence containing both D- and L-amino acids, or an amide thereof, such as an amide derived from ammonia, an (1–4C)alkylamine (such as methylamine) or a di(1–4C)alkylamine (such as dimethylamine). A particular group of values for R$^4$ includes, for example, those values defined herein where R$^4$ is not a sequence of 1 to 6 amino acids.

A preferred value for R$^4$ includes, for example, 4-carbamoyl-1-piperidyl (the residue of piperidine-4-carboxamide (Pip-NH$_2$)), 4-carboxy-1-piperidyl (the residue of piperidine-4-carboxylic acid (Pip-OH)), 4-(carbamoylmethyl)anilino (the residue of 4-aminophenylacetamide (Papa-NH$_2$)), 4-(carboxymethyl) anilino (the residue of 4-aminophenylacetic acid (Papa-OH)) and 4-(2-guanidinoethyl)anilino (the residue of 2-(4-aminophenyl)ethylguanidine (Pape-NHC(=NH)NH$_2$).

A particular group of values for R$^4$ includes, for example Pip-NH$_2$, Papa-NH$_2$, Pape-NHC(=NH)NH$_2$ and NHRc in which Rc is 3-guanidinopropyl, 2-morpholinoethyl or 4-(2-(2-hydroxyethoxy)ethyl-1-piperazinyl.

A preferred value for R$^2$ includes, for example, a group of the formula II, especially IIa and more especially IIb.

A preferred group of peptide derivatives of formula I includes, for example, peptide derivatives in which R$^1$ is a sequence of five L-amino acids and R$^3$ is a single L-amino acid, which sequence R$^1$ and R$^3$ have any of the values defined above, including the particular and preferred values for R$^1$ and R$^3$. Within this group, a sub-group of particularly preferred peptide derivatives includes, for example, those in which $R^2$ is a group of the formula II, especially IIa and more especially IIb. A further sub-group of particularly preferred peptide derivatives includes, for example, those in which $R^4$ is -Pip-OH, -Pip-NH$_2$, -Papa-OH or Papa-NH$_2$. An especially preferred subgroup of compounds includes, for example, those in which $R^3$ taken together with $R^4$ is Ala-Pip.NH$_2$ or Ala-Papa-NH$_2$.

A further preferred group of peptide derivatives of the invention include, for example, those in which $R^1$ is a sequence of 5 L-amino acids represented as AA1-AA2-AA3-AA4-AA5 in which:

AA1 is selected from Ala, Ile, Tyr, Val, Glu, Lys, Arg, Gly, Gap, GapMe$_4$ and 3,3,3-trifluoroalanine, particularly Ala, Ile, Arg, Gap and GapMe$_4$, especially Ala, Arg and GapMe$_4$ and more especially Ala and Arg;

AA2 is selected from Ala, Lys, Glu, Sar, Val, Arg, Gly, Pro,Ile, Tic, 3,3,3-trifluoroalanine and $N^6$-diethylLys, particularly Ala, Arg, Ile, Lys and Tic, especially Ala, Arg, Lys and Ile and more especially Ala and Arg;

AA3 is selected from Ala, His, Gln, Val, Thr, Glu, Gly, Asp, Asn and $N^3$-diethylDap, particularly Ala, His, Asp and Asn, especially Ala and Asn and more especially Ala;

AA4 is selected from Ala, Lys, Asn, Arg, Thr, Glu, Sar, Gly, Pro, His and $N^6$-diethylLys, particularly Ala, Arg, Lys and His, especially Ala, Arg and His and more especially Ala; and AA5 is selected from Thr, Val, Ala, Gly, Dap, Dab, Pro, Hyp, Asn and $N^3$-diethylDap, particularly Thr, Val and Dap and especially Thr and Val; and $R^3$ is a single L-amino acid selected from Ala, Gly, Dap, azaalanine and azaglycine, particularly Ala, Gly and azaglycine, especially Ala and Gly and more especially Ala; and wherein P, $R^2$ and $R^4$ have any of the values, including the particular and preferred values. defined above. Within this group, a particular sub-group of compounds include, for example, those in which the sequence AA1-AA2-AA3-AA4-AA5 is selected from Ala-Ala-Ala-Lys-Val (SEQ ID NO:37), Ile-Ala-Ala-Arg-Thr (SEQ ID NO:45), Arg-Ala-Ala-Ala-Val (SEQ ID NO:46), Arg-Ala-Ala-Ala-Thr (SEQ ID NO:47), Ala-Ala-Ala-Arg-Val (SEQ ID NO:39), Ala-Arg-Ala-Arg-Val (SEQ ID NO:42), Ala-Ile-Ala-Arg-Val (SEQ ID NO:50), Ala-Arg-Ala-His-Val (SEQ ID NO:51), Ala-Ala-Asn-Arg-Val (SEQ ID NO:53), Ala-Arg-Ala-Ala-Thr (SEQ ID NO:52), Ala-Arg-Ala-Arg-Thr (SEQ ID NO:49), Gap-Ala-Ala-Ala-Thr (SEQ ID NO:54), GapMe$_4$-Ala-Ala-Ala-Thr (SEQ ID NO:55) and Ala-Ala-Ala-Arg-Thr (SEQ ID NO:48). Compounds in which $R^4$ is Pip-NH$_2$, Papa-NH$_2$ and Pape-NHC(=NH)NH$_2$ are preferred.

A further preferred group of peptide derivatives of the invention include, for example, those in which $R^1$ is a sequence of 3 L-amino acids represented as AA1-AA2-AA3 in which:

AA1 is selected from Ala, Ile, Tyr, Val, Glu, Lys, Arg, Gly, Gap, GapMe$_4$ and 3,3,3-trifluoroalanine, particularly Ala, Ile, Arg, Gap and GapMe$_4$, especially Ala, Arg and GapMe$_4$ and more especially Ala and Arg;

AA2 is selected from Ala. Lys, Glu, Sar, Val, Arg, Gly, Pro, Ile, Tic, 3,3,3-trifluoroalanine and $N^6$-diethylLys, particularly Ala, Arg, lIe, Lys and Tic, especially Ala, Arg, Lys and Ile and more especially Ala and Arg;

AA3 is selected from Ala, His, Gln, Val, Thr, Glu, Gly, Asp, Asn and $N^3$-diethylDap, particularly Ala, His, Asp and Asn, especially Ala and Asn and more especially Ala; and $R^3$ is a sequence of 3 L-amino acids represented as AA6-AA7-AA8 in which:

AA6 is selected from Gly, Leu, Lys, Ala, Pro, Glu, Sar, His and Dap, particularly Ala, Leu and Pro and especially Ala.:

AA7 is selected from Pro, Ala, Lys, Arg, Glu, Sar, Gly, Oic and Dic, especially Ala and Arg; and AA8 is selected from from Ala, Gly, Dap, azaalanine and azaglycine, particularly Ala, Gly and azaglycine and especially Ala; and P, $R^2$ and $R^4$ have any of the values, including the particular and preferred values, defined above. Within this group, a particular sub-group of compounds includes, for example, those compounds in which the sequence AA1-AA2-AA3 is selected from Ala-Lys-Ala and Ala-Arg-Ala and the sequence AA6-AA7-AA8 is selected from Ala-Ala-Ala and Ala-Arg-Ala. Compounds in which $R^4$ is Pip-NH$_2$, Papa-NH$_2$ and Pape-NHC(=NH)NH$_2$ are preferred.

A preferred aspect of the present invention comprises peptide derivatives of the formula I, in which $R^2$ is a group of the formula II (and especially wherein A is methylene), and more especially IIb, and P, $R^1$, $R^3$ and $R^4$ have any of the values, including the particular and preferred values, defined above.

A further preferred aspect of the present invention comprises peptide derivatives of the formula I which contain an arginine residue, particularly compounds in which the first amino acid residue of $R^1$ (as read from left to right) when it is a sequence of 5 L-amino acids is arginine (such as Arg-Ala-Ala-Ala-Val (SEQ ID NO:46) and Arg-Ala-Ala-Ala-Thr(SEQ ID NO:47)) and compounds in which the second amino acid residue of $R^1$ when it is a sequence of 3 L-amino acids is arginine and/or the second amino acid residue of $R^3$ when it is a sequence of 3 L-amino acids is :arginine (such as when $R^1$ is Arg-Ala-Ala and $R^2$ is Ala-Ala-Ala or when $R^1$ and $R^2$ are both Ala-Arg-Ala.)

A further aspect of the present invention comprises peptide derivatives of the formula I in which $R^2$ is a group of the formula IIIa or IIIb and P, $R^1$, $R^3$ and $R^4$ have any of the values, including the particular and preferred values, decribed above.

Compounds of the invention which are of particular interest include, for example, the specific embodiments set out hereinafter in the accompanying Examples. Of these, the compounds of Examples 5, 16, 19, 23 and 24 are of special importance and these compounds, or a pharmaceutically acceptable salt thereof, are provided as further features of the invention.

(SEQ ID NO: 5)

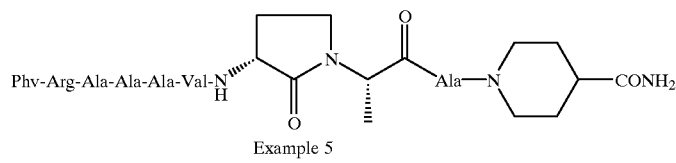

Example 5

-continued (SEQ ID NO: 17)

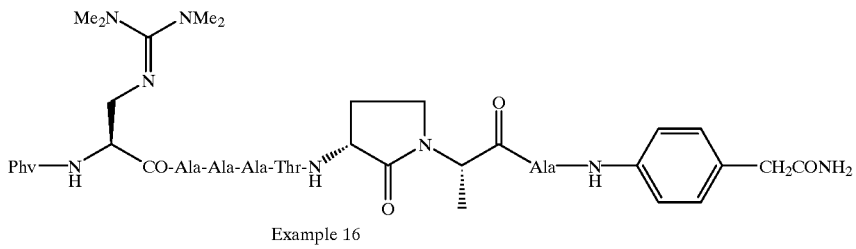

Example 16

(SEQ ID NO: 20)

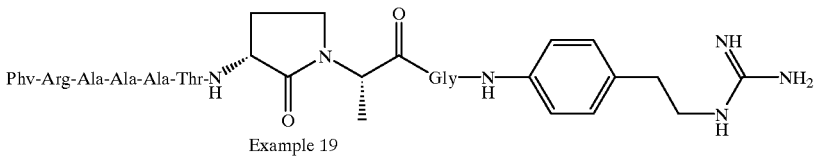

Example 19

(SEQ ID NO: 24)

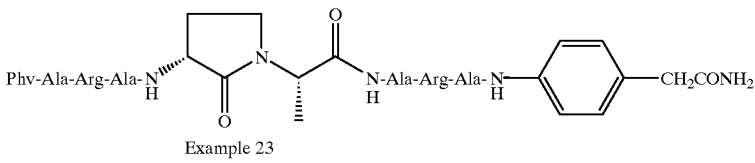

Example 23

(SEQ ID NO: 25)

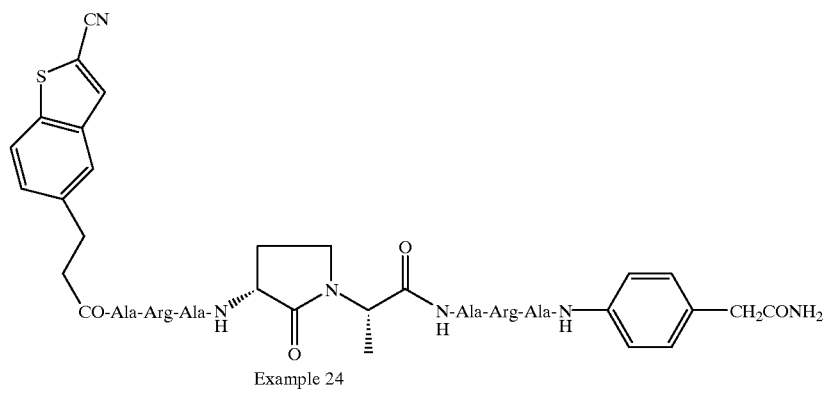

Example 24

Pharmaceutically acceptable salts include, for example, for peptide derivatives that are sufficiently basic, for example those having a free amino group, salts with acids forming physiologically acceptable anions, such as salts with mineral acids, for example, hydrogen halides (such as hydrogen chloride and hydrogen bromide), sulphonic and phosphonic acids, and with organic acids such as acetic, oxalic, tartaric, mandelic, p-toluenesulphonic, methanesulphonic acids, trifluoroacetic and the like, and for peptide derivatives that are sufficiently acidic, for example those having a free carboxylic acid group, salts with bases forming physiologically acceptable cations, such as salts with alkali metal (such as sodium and potassium), alkaline earth metal (such as magnesium and calcium), aluminium and ammonium salts, as well as salts with suitable organic bases such as ethanolamine, methylamine, diethylamine, isopropylamine, trimethylamine and the like.

As stated above, the peptide derivatives of formula I, or a pharmaceutically acceptable salt thereof, will have beneficial pharmacological effect in warm-blooded animals (including man) in a range of autoimmune diseases or medical conditions, to treat symptoms or as a disease modifying agent or as a prophylactic treatment. Such diseases may include, for example, rheumatoid arthritis, multiple sclerosis, Goodpasture's syndrome, idiopathic thrombocytopenic purpura, juvenile rheumatoid arthritis, coeliac disease, systemic lupus erythematosus, ankylosing spondylitis, Sjogren syndrome, myasthenia gravis; Type I (insulin dependent) diabetes, Hashimoto's disease, Grave's disease, Addison's disease, scleroderma, polymyositis, dermatomyositis, pemphigus vulgaris, bullous pemphigoid autoimmune haemolytic anaemia, pernicious anaemia, glomerulonephritis, graft rejections and such like, especially rheumatoid arthritis and multiple sclerosis.

The utility of the peptide derivatives of the formula I, or a pharmaceutically acceptable salt thereof, may be assessed using a variety of standard tests and clinical studies, including those described in International Patent Application, Publication Nos. WO92/02543, WO93/05011 and WO95/07707 (or modifications thereof) and those described below. The peptide derivatives of formula I show significant activity in one or more of such tests or studies.

Test A: Purified HLA-DR peptide in vitro binding assay. (This assay may be used to demonstrate the binding of the peptide derivatives of formula I to disease-associated MHC class II molecules.) 30 $\mu$l of biotin-FHA$_{307-320}$ (FHA (307–320) peptide, derivatised with long-chain biotin at the N-terminus, Biotin-Ahx-Pro-Lys-Tyr-Val-Lys-Gln-Asn-Thr-Leu-Lys-Leu-Ala-Thr-Gly-OH (SEQ ID NO:60)) at 800 nM in phosphate buffered saline solution (PBS) is incubated with 30 µL of purified HLA-DR4Dw4 at a concentration between 0.5 and 5 µg/ml in V-welled micro-titre plates (Nunc) for 48 hours with or without inhibitor peptides. At the end of the incubation period 100 µl of the incubate is transferred to Enzyme Linked lmmunoSorbant Assay (ELISA) plates (Nunc) previously coated with an anti-MHC antibody (L243—American Type Culture Collection (ATCC) HB55 —as described in Lampson and Levy (1980) J. Immunol. 125, 293–299) at a concentration of 10 µg/ml for 1 hour at room temperature and blocked thereafter for 1 hour with 1% bovine serum albumin (BSA) in PBS and 0.05% Tween 20. After a further 1 hour period the unbound peptide is washed away and a 1/4,000 dilution of streptavidin peroxidase (Sigma) in PBS with 0.01% of a suitable detergent such as NP40 (Sigma) added for 2 hours at room temperature. After further washing, tetramethylbenzidene (TMB) substrate solution (1 TMB tablet (Sigma) in 10 mls of 0.1 M citrate/acetate buffer, pH 6.0 with 36 µl urea hydrogen peroxide (UHPO) (Fluka)) is added to each of the plates. The reaction is stopped by adding 2M sulphuric acid (10 µl per well) and the absorbance read at 450 nm to quantify the amount of peptide bound. The inhibitory activity of peptides is obtained by plotting absorbance against concentration.

The purified HLA-DR4Dw4 may be obtained as follows:
(i) Expression of HLA-DR in the Baculovirus System The expression of recombinant proteins in insect cells from baculovirus vectors is an established procedure to obtain high yields of recombinant protein [Luckow, V A & Summers, M D, 1988, Biotechnology, 6, 47–551]. To enable the expression of the heterodimeric HLA-DR, eg. HLA-DR4Dw4, from a single recombinant baculovirus vector (as opposed to having separate recombinant viruses for the α and β chains and then doing a co-infection), a double-recombinant baculovirus is constructed which carries both the α and β chains.

A cDNA encoding the sequence of the α polypeptide is cloned into the transfer vector pacYM1 [Matsuura, Y; Possee, R D; Overton, H A & Bishop, D H L, 1987, J. Gen. Virol., 68, 1233–1250] to place expression of the protein under the control of the polyhedrin promoter. The unit is inserted into the baculovirus genome by homologous recombination in Sf21 insect cells to create a single recombinant baculovirus for the α chain. The techniques for the culture and infection of insect cells, for the homologous recombination and detection/isolation of recombinant viruses are all fully described by Summers, M D D & Smith G E (1987) [A Manual of Methods for Baculovirus Vectors and Insect Cell Culture Procedures; Texas Agricultural Experiment Station, Bulletin No. 1555]. The molecular genetic techniques used to construct the recombinant vectors are likewise readily available in the literature and are most fully described by Sambrook, J; Fritsch, E F & Maniatis T, (1989) [Molecular Cloning. A Laboratory Manual. 2nd Edition. Cold Spring Harbor Laboratory Press].

To create the double-recombinant baculovirus, a cDNA encoding the β chain is cloned into the transfer vector pAcUW1 [Weyer, U; Knight, S & Possee, R D, 1990, J. Gen. Virol., 71, 1525–1534] to place expression of the protein under the control of the P10 promoter. The unit is then inserted into the genome of the single recombinant baculovirus carrying the α chain. Double-recombinant viruses are detected by spotting insect cells, infected with randomly picked viruses from the transfection, onto membranes and reacting them with a monoclonal antibody, e.g. L243, which specifically recognises the HLA-DR heterodimer. Binding of the antibody to Sf21 insect cells is detected using standard flow cytometry techniques, readily available in the literature. Stable, double-recombinant baculovirus expressing HLA-DR are plaque-purified.

(ii) Purification of HLA-DR from Insect Cells

The method used is a modification of that described by Gorga et al 1987. (Gorga et al 1987. J. Biol. Chem. 262, 16087–16094). HLA-DR expressing baculovirus/Sf21 cells (10L which is approximately equal to $2 \times 10^{10}$ cells) are solubilised in 100 ml of 5 mM EDTA (sodium salt), 50 mM Tris-HCL pH 8.5, 2% NP40, 150nM NaCl, 1 mM iodoacetamide. ImM PMSF by homogenisation with 10 strokes of a teflon glass homogeniser. The homogenate is spun at 100,000 g for 1 hour and the supernatant collected. The anti-HLA-DR monoclonal antibody LB3.1 (Gorga et al 1986, Cell. Immunol. 103, 160–172) covalently coupled to a ratio of 50 mg of L243 to 10 ml of Protein A-Sepharose fast flow (Pharmnacia) and pre-incubated with 10 mM Tris-HCl, pH 8.0, 0.1% NP-40 is incubated overnight with the supernatant. The resin is then put into a column and washed with 10 mM Tris-HCl, pH 8.0, 0. 1% NP-40 (20 column volumes) followed by 0.15 M NaCl, 50 nM $Na_2HPO_4$, pH 7.0 1% octylglucoside (20 column volumes). The HLA-DR is eluted with 50 mM diethylamine pH 11.0, 0.15 M NaCl, 1% octylglucoside. Column fractions are immediately neutralised with 1 M Tris-HCl pH 8.0 and concentrated by ultracentrifugation through a centricon-10 membrane. Protein content is determined by a BCA protein assay (Pierce) and purity by SDA-PAGE electrophoresis.

In general, the peptide derivatives of formula I as defined above which were tested in test A showed significant inhibition at a concentration of about 10 µM or much less.

A further preferred aspect of the present invention comprises a peptide derivative of the formula I, or a pharmaceutically acceptable salt thereof, which does not bind to HLA-DR3 but binds to HLA-DR1 and/or HLA-DR4Dw4 and/or HLA-DR4Dw14. HLA-DR3 is a common HLA-DR allele which is not associated with rheumatoid arthritis. Accordingly, in rheumatoid arthritis patients who carry HLA-DR3 as one of their alleles (which is approximately one third of the total rheumatoid artritis patients), such a peptide derivative of the formula I will not interfere with the normal role of HLA-DR3 in the host-defense function. The use of such a peptide derivative is therefore particularly advantageous for treating rheumatoid arthritis patients as it will result in less immunosuppression than would occur with a non-selective DR binder.

As a variant to test A, the ability of a peptide of the invention to bind to one or more HLA-DR molecules was assessed as follows:

(i) Purification of HLA-DR Types from Cell Lines

The method used was a modification of that described by Gorga et al, 1987, J.Biol.Chem. 262, 16087–16094. Human HLA-DR antigens were purified from various cell lines by immunoaffinity chromatography. Briefly, $1 \times 10^9$–$5 \times 10^9$ pelleted cells of the appropriate cell line selected from Hom 2 (source of DR1), BBF (source of DR2), AVL-B (source of DR3), JAH (source of DR4Dw4), JHAF (source of DR4Dw13) or PE117 (source of DR4Dw14) were solubilised at approximately 4° C. in 50 ml of 5 mM EDTA (sodium salt), 50 mM Tris-HCL pH 7.4, 2% NP40, 150 mM NaCl, 1 mM iodoacetamide, 1 mM PMSF, by homogenisation with 10 strokes of a teflon glass homogeniser. The homogenate was spun at 100,000 g for 1 hour and the supernatant collected. The anti-HLA-DR monoclonal antibody LB3.1 (Gorga et al, 1986, Cell.Immunol., 103, 160–173) covalently coupled to CNBr-Sepharose 4B (Pharnacia) was pre-equilibrated with 150 mM NaCl, 50 mM Tris-HCL, pH 7.4, 0.1% NP-40 and incubated overnight with the supernatant. The resin was then packed in a column and washed with 0.15 M NaCl, 50 mM Tris-HCL, pH 7.4, 1% octylglucoside (20 column volumes). The HLA-DR was eluted with 50 mM diethylamine pH 11.0, 0.15 M NaCl, 1% octylglucoside. Column fractions were immediately neutralised with 0.5 M HEPES NaOH pH 7.4. Protein content was determined by a Biorad protein assay and purity by SDS-PAGE electrophoresis.

(ii) Peptide Selectivity Binding Assays 200 nM biotin-FHA$_{307-320}$ in phosphate buffered saline (PBS) was incubated with either purified HLA-DR1, DR2, DR4Dw4, DR4Dw13 or DR4Dw14, (2–20μg/ml) in V-well microtitre plates (Nunc) with or without inhibitor peptides in assay buffer (PBS, 0.01% NP40 (Sigma.)) For DR3 inhibition, 400 nM Biotin-Ahx-(D)Ala-Ala-Ala-Che-Ile-Ala-Ala-Ala-Thr-Leu-Lys-Ala-Ala-(D)Ala-OH was incubated with purified DR3 (20 μg/ml.), and incubated as above. After 48 hours, the incubates were treated, and absorbance readings taken as described in Test A. The inhibitory activity of peptides, expressed as IC$_{50}$ values, was calculated using Microcal Origin software on a PC.

Test B: Inhibition of T cell activation in vitro. (This assay may be used to demonstrate the ability of the peptide derivatives of formula I to inhibit a T cell immune response mediated by or through an MHC class II molecule).

Inhibitor peptides were tested for the ability to block stimulation of the B52.24 murine T cell hybridoma line which responds to the FHA$_{307-320}$ peptide (H-Pro-Lys-Tyr-Val-Lys-Gln-Asn-Thr-Leu-Lys-Leu-Ala-Thr-Gly-OH (SEQ ID NO:61)) presented by HLA-DR4Dw4 molecules. B52.24 was produced by the fusion of lymph node T cells taken from FHA$_{307-320}$ immunised HLA-DR4Dw4 transgenic mice (International Patent Application, Publication No WO95/03331) with the BW5147 murine T cell lymphoma line (White et al (1989) J. Immunol. 143, 1822) as outlined in Woods et al (1994) J. Exp. Med. 180, 173–181 and following the general methods for the generation of T cell hybridomas given in Current Protocols in Immunology, Volume 2, 7.21.

Inhibitor peptides at concentrations between 100 and 0.1 μM (or lower) were mixed with the antigenic peptide FHA$_{307-320}$ in either varying concentrations between 100 and 0.1 μM or at a fixed concentration of 10 μM by dilution in RPM1-1640 culture media (Gibco) in a 96-well mictrotitre plate (Nunc) in a final volume of 100 μl. HLA-DR4Dw4 expressing B cells such as the JAH EBV transformed lymphoblastoid cell line (European Culture Collection ECACC 85102909) or B cells taken from an HLA-DR4Dw4 homozygous individual and transformed with Epsten Barr virus according to the method described in Current Protocols in Immunology 7.22.1 were fixed using gluteraldehyde by suspension in 1% gluteraldehyde (Sigma) at 4×10$^6$ cells/ml for 30 seconds, after which an equal volume of 200 mM lysine (Sigma) was added for 3 minutes. The cells were recovered by centrifugation at 300g, washed in RPMI-1640 and added to the microtitre plates containing antigen and inhibitor compounds at a concentration of 2×10$^5$ cells per well. The microtitre plates were incubated for 2 hours at 37° C. and 5% CO$_2$.

The microtitre plates were then washed in RPMI-1640 by centrifugation at 300 g and aspirated twice before the addition of the B52.24 T cell hybridoma line at a concentration of 10$^5$ cells per well in culture medium (RPMI-1640, 10% foetal calf serum (Gibco) and 2 mM glutamine (Gibco)). The microtitre plates were then incubated for a further 2 days at 37° C. and 5% CO$_2$. The plates were then centrifuged at 300 g for 10 minutes and 150 μl of supernatant removed from all wells to be frozen at −20° C. prior to bioassay for IL-2 content.

The culture plates containing supernatants to be assayed were left at room temperature to thaw and 100 ml of supernatant was transferred to fresh 96 round bottomed well plates. 1:1 senal dilutions of IL-2 were carried out using culture media (RPMI-1640 (Gibco), 10% foetal calf serum (Advanced Protein Products), 100 μg/ml streptomycin and 100 U/ml penicillin (Gibco), 2 mM L-glutamine (Gibco) and 50 μM 2-mercaptoethanol (Sigma)), to produce a standard curve of 250 units/ml to 0.04 units/ml IL-2 final. An IL-2 dependent cell line such as CTLL-2 cells (Nature (1977) 268 154–156) or HT-2 cells (J. Irnmunol. Methods (1987) 94–104) were harvested and washed twice using culture media prior to resuspension at 5×10$^4$ cells/ml. 100 μl of IL-2 dependent cell suspension was added to each well of the standard curve and test samples. The culture plates were incubated for 72hrs at 37° C. and 5% CO$_2$. After which, 20 μL (1 mCi) of 3H-Thymidine (Amersham International) was added to each well and the plates returned to the incubator for a further 16 hrs. The contents of each plate were harvested onto glass fibre filter mats and the radioactivity measured using a betaplate scintillation counter.

In general, the peptide derivatives of formula I as defined above which were tested in test B showed significant inhibition at a concentration of about 10 μM or much less.

Test C: Peptide stimulated DTH (delayed type hypersensitivity) in BALB/C mice. (The assay may be used to demonstrate in vivo activity of peptide derivativesof formula I in an animal model). Balbic female mice (18–20g), 5 per group, were immunised sub-cutaneously on the flank with 0.1 ml of an emulsion of ovalbumin (Sigma) (2mg/ml in saline) mixed 1:1 (v/v) with complete Freunds adjurant (Sigma). Seven days later footpad thickness was detemined using a dual caliper micrometer followed by a challenge in one hind footpad with a 30 μl sub-plantar injection of 1% heat-aggregated ovalbumin protein in saline. Twenty-four hours after antigen challenge, footpads were measured and the DTH response calculated as the percentage increase in footpad thickness in the injected footpad compared to contralateral control. Inhibitors were administered by 3-day osmotic mini-pumps (Alzet) implanted 24 hours prior to antigen challenge at doses ranging from 10 mg/kg/day to 0.1 μg/kg/day. The degree of inhibition was calculated by substracting the value for swelling of inhibitor treated footpads from that of the vehicle dosed controls, dividing by the control value and multiplying by 100%.

In general, the peptide derivatives of formula I as defined above which were tested in Test C showed significant inhibition at a dose of about 1 mg/kg/day or much less, without any overt toxicological or other untoward pharmacological effect.

Test D: (This assay may be used to demonstrate in vivo activity of peptide derivatives of formula I in an animal model of arthritis).

Balbic female mice (19–21 g, 5–10/group) are immunised on day 0 and boosted on day 7 with a sub-cutaneous injection of 0.1 ml of an emulsion containing equal volumes of 2 mg/ml methylated bovine serum albumin (met-BSA, Sigma) in saline and complete Freund's adjuvant (Sigma) supplemented with 2.5 mg/ml *Mycobacterium tudercolosis* (MTB, strains C, DT and PN, MAFF, Weybridge, Surrey) thus giving a final MTB concentration of 3.5 mg/ml. An additional 0.1 ml i.p injection of 10$^9$ *Bordetella pertussis* organisms (Wellcome Pertussis vaccine) in saline is given at the same time. Fourteen days later, animals are challenged into one knee joint with a 10 μl intra-articular injection containing 100 μg of met-BSA in saline using a 30 G needle and hamilton syringe. The contralateral knee is injected with a similar volume of saline and serves as a control. The degree of inflammation/swelling associated with both knees is determined 13 days later by measuring using a dual-caliper micrometer. This is achieved by making an incision with blunt-ended scissors and forceps into the skin approximately 5mm above and below the knee and continuing along the side of the knee to form a flap which is then carefully cut away to expose the underlying joint. Measurements are made across the widest part of the knee, in the horizontal plane, on the flexed limb held in a fixed position. Percentage increase in inflammation in the antigen-injected knee compared to control is calculated according to the formula: [antigen-injected knee thickness—saline-injected knee thickness/saline-injected knee thickness]×100. Inhibitors are administered using 14 day osmotic mini-pumps (Alzet) implanted 24 hrs before antigen challenge at does ranging from 10 mg/kg/day to 0.1 ug/kg/day. The percentage inhibition of inflammation/swelling is calculated from the thickness measurements by subtracting the value for swelling in the inhibitor-treated group from that of the vehicle dosed controls, dividing by the control value and multiplying by 100. Additional assessments of disease involve 1) the histological evaluation of inflammation, synovitis and cartilage/bone erosions carried out on fixed knee sections stained with haemotoxylin and eosin and 2) the determination of levels of acute phase reactants in serum, serum amyloid P and/or haptoglobin.

Peptide derivatives of formula I as defined above may show in Test D significant inhibition at a dose of about 10 mg/kg/day or much less.

By way of illustration of the pharmacological activity of particular peptide derivatives of the formula I, the compounds of Examples 5, 16 and 23 all showed significant binding to HLA-DR4Dw4 in Test A at a concentration of<0.1 micromolar, and were active at<0.1 mg/kg/day in Test C. These compounds also showed good aqueous stability at pH3 and pH 7.6 and, in the form of an extruded polymer depot formulation, showed minimal loss due to degradation on extrusion and minimal degradation on release from such a depot formulation. In the variant to Test A, the compound of Example 23 was shown to bind significantly to HLA-DR1, HLA-DR2, HLA-DR4Dw4 and HLA-DR4Dw14 but did not bind significantly to HLA-DR3 ($IC_{50}$>100 micromolar).

A peptide derivative of formula I may be prepared by any process well known in the art of peptide chemistry to be applicable to the synthesis of analogous peptides.

A peptide derivative of formula I may be obtained, for example, by procedures analogous to those disclosed in "Solid Phase Peptide Synthesis: A practical approach" by Atherton and Sheppard (published by IRL press at Oxford University Press, 1989). "Solid Phase Peptide Synthesis" by Stewart and Young (published by the Pierce Chemical Company, Illinois, 1984), "Principles of Peptide Synthesis" (published by Springer-Verlag, Berlin, 1984), and a series of books "Amino Acids, Peptides and Proteins" (volumes 1–25; volume 25 published in 1994) (published by the Royal Society of Chemistry, Cambridge, UK).

Preferably, a peptide derivative of formula I is prepared by solid phase sequential synthesis. Using this technique, the amino acid which is to become the C-terminus amino acid of the peptide is protected at the alpha-amino group, and, if necessary, in the side chain and coupled to a solid support, for example a resin, such as 2-chlorotritylchloride resin or Merrifield resin (chloromethylpolystyrene-divinylbenzene) if a free carboxylic acid is required after cleavage, or Rink Amide resin (4-(2',4'-dimethoxyphenyl-Fmoc-aminomethyl)-phenoxy resin) or Rink Amide MBHA resin (N-(4-(2',4'-dimethoxyphenyl-Fmoc-aminomethyl)-phenoxyacetamido-norleucyl)4-methyl benzhydrylamine resin) (all available from Calbiochem-Novabiochem) if a carboxamide is required after cleavage, whereafter the protecting group on the alpha-amino group is removed. The amino acid which is to be attached to the C-terminus amino acid is protected at the alpha-amino group and, if necessary, in the side chain and coupled to the C-terminus amino acid which remains attached to the solid suppon. The stepwise process of deprotection of the alpha-amino group and coupling to the next amino acid is repeated to give a protected or unprotected polypeptide attached to the solid support. The group $R^2$ of formula II or III is incorporated into the sequence by using an appropriately protected (3-amino-2-oxo-pyrrolidin-1-yl)alkanoic acid (for a peptide derivative containing II in which A=methylene) or a corresponding oxa analogue obtained as described in *J. Med. Chem.*, 1993, 36, 256–263 or by analogy therewith (for a peptide derivative containing II in which A is oxygen) or an (6-oxo-1,7-diazaspiro[4.4]non-7-yl)alkanoic acid (for a peptide derivative containing III) in place of a protected amino acid. The protected or unprotected polypeptide is released from the solid support by standard procedures, for example using a mixture of trifluoroacetic acid, triethylsilane and water. It will be appreciated that a side-chain protecting group may be cleaved under the conditions used to release the peptide from the solid support, or may be cleaved as a separate step prior or subsequent to release of the peptide from the solid support. It will also be appreciated that the procedure to build up the polypeptide may be modified by using a sequence of two or more suitably protected amino acids in a particular coupling step. The synthesis may use manual techniques or be carried out automatically, employing for example, an Applied Biosystems 431A or 430A peptide synthesiser an Advanced Chemtech ACT357 peptide synthesiser or similar automatic peptide synthesiser, or a combination of both techniques may be used.

During the assembly of the peptides, the amino acid functional groups not taking part in the reaction are protected by various functional groups. For example, the N-terminal and side chain amino groups may be protected by using 9-fluorenylmethoxycarbonyl (Fmoc), t-butoxycarbonyl (Boc), biphenylisopropoxycarbonyl (Bpoc), 2-[3,5-dimethoxyphenyl]propyl-2-oxycarbonyl (Ddz), adamantyloxycarbonyl (Adoc), allyloxycarbonyl (Aloc), 2,2,2-trichloroethoxycarbonyl (Troc), benzyloxycarbonyl and various substituted benzyloxycarbonyl groups. These protecting groups can be cleaved when required by the standard techniques (e.g. acid or base treatment, catalytic hydrogenolysis and Pd(0) treatment or zinc/acetic acid treatment).

Suitable protecting groups used for the protection of the side chain guanidino group in the peptides containing an arginine residue include a nitro, adamantyloxycarbonyl, 4-methoxy-2,3,6-trimethylbenzenesulphonyl (Mtr), 2,2,5,7,8-pentamethylchroman-6-sulphonyl (Pmc) and (especially) 2,2,4,6,7-pentamethyldihydrobenzofuran-5-sulphonyl (Pbf) group.

Suitable protecting groups used for the protection of a side chain hydroxy group include t-butyl, benzyl and trityl (Trt). Suitable protecting groups used for the side chain imidazole group in the peptides containing a histidine residue, include a trityl, benzyl, tosyl, dinitrophenyl, Adoc, Boc or Fmoc group.

Suitable protecting groups used for the protection of a side chain carboxyl group include various esters (e.g. methyl, ethyl, t-butyl, benzyl, nitrobenzyl allyl and 9-fluorenylmethyl).

The protecting group cleavage reactions can be performed at temperatures in the range of 40° C. to 40° C. (preferably at or about ambient temperature) and over a period of time in the range of 10 minutes to 24 hours.

Suitable coupling methods used for the coupling of the individual amino acids include the commonly used azide, symmetrical anhydride, mixed anhydride and various active esters and carbodiumides. In the case of various carbodiimides (e.g. dicyclohexyl- or diisopropyl-carbodiumides), a number of additives (e.g. 1-hydroxybenzotriazole (HOBT) and N-hydroxysuccinimde) may also be added. In addition, the amino acid couplings can also be achieved by using a number of other reagents, e.g. 1H-benzotriazole-1-yl-oxytris-pyrrolidinophosphonium hexafluorophosphate (PyBOP), (2-(1H-benzotriazole-1-yl)-1,1,3,3-tetramethyluronium tetrafluoroborate (TBTU) and (2-(1H-benzotriazole-1-yl)-1,1,3,3-tetrarnethyluronium tetrafluoroborate (HBTU). The coupling reactions can be performed at temperatures in the range of −20° C. and 40° C. and over a period of time in the range of 10 minutes to 24 hours. A suitable medium for carrying out the coupling reactions includes, for example, N,N-dimethylformamide (DMF). A particularly suitable method includes the use of HBTU, HOBT and diisopropylethylamine in DMF.

These and other methods of peptide synthesis are exemplified in the International Patent Applications referred to herein. A hydrophobic residue P which is a group of the formula R—, R.CO—, R.SO$_2$—, R.O.CO—. R.NHCO—, R.O.CS—, R.S.CO—, R.NHCS—, R.S.CS— and R.CS— (or such a group present as a substituent on a terminal amino group of P where P is a hydrophobic amino acid or a hydrophobic amino acid bearing further amino acids) may be incorporated, for example, as a final step by alkylation, acylation or other standard functional group modification of a terminal amino group (for example prior to or subsequent to release of the peptide from a support). When C-terminus modifications are required (to obtain a particular value for $R^4$), they may be performed after the peptide is synthesised, by conventional fuictional group modification or appropriate choice of the initial starting resin or the protected entity first coupled to the resin (for example by using a suitably protected group of the formula $R^4$—H). Typical examples of the preparation of peptide derivatives of formula I are provided in the examples hereinafter.

A typical procedure for measuring the stability of a peptide derivative of the present invention is as follows, in which, to minimize microbial contamination and degradation, all equipment that is used to prepare peptide solutions is sterilized in an autoclave and all material transfers carried out in a Class II laminar flow cabinet. Approximately 20 ml of McIlvaine's citric acid-phosphate buffer solution at pH 3 or 7.6 containing 0.02% sodium azide is filtered into a 50 mL bottle using a sterile 0.22 μm filter unit and a 20 ml syringe. Approximately 1.2 mg of peptide is accurately weighed in a capped vial. Using a sterile pipette tip, sufficient buffer solution is added to the peptide in the vial to give a peptide concentration of 0.1 mg/ml. The vial is capped and shaken to dissolve the peptide. Using a sterile pipette tip, aliquots of approximately 1 ml of the peptide solution are transferred to 10 HPLC vials, which are then capped. 5 vials are stored at −18 and 37° C. The area of the peptide peak for the solution is determined by HPLC using appropriate standards initially and after storage at −18 and 37° C. for 1, 2, 3 and 4 weeks, using a fresh vial at each time point with duplicate sample injections. The percentage of peptide remaining after storage at 37° C. at each time point is determined from the ratio of the area of the peptide peak at each time point to the initial area. Preferred peptide derivatives of the present invention have greater than 90%, and preferably greater than 95%, of peptide remaining after storage at 37° C. at both pH 3 and 7.6.

The peptide derivative of formula I will generally be administered for therapeutic or prophylactic purposes to warm-blooded animals (including man) requiring such treatment in the form of a pharmaceutical composition, as is well known in the pharmaceutical art.

According to a further feature of the invention there is provided a pharmaceutical composition which comprises a peptide derivative of the formula I, or a pharmaceutically acceptable salt thereof, in association with a pharmaceutically acceptable diluent or carrier.

The composition may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example as a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. The composition may be in a form suitable for topical administration such as for example creams, ointments and gels. Skin patches are also contemplated. Formulation in general is described in Chapter 25.2 of Comprehensive Medicinal Chemistry, Volume 5, Editor Hansch et al, Pergamon Press 1990.

In general the above compositions may be prepared in a conventional manner using conventional excipients. However, in the case of a composition for oral administration, it may be convenient for the composition to include a coating to protect the polypeptide active ingredient from the actions of enzymes in the stomach.

A preferred composition of the invention is one suitable for oral adminstration in unit dosage form for example a tablet or capsule which contains from 2.5 to 500 mg, and preferably 10 to 100 mg, of polypeptide in each unit dose, or one suitable for parenteral administration which contains from 0.5 to 100 mg of polypeptide per ml, and preferably 1 to 10 mg of polypeptide per ml of solution.

A parenteral composition is preferably a solution in isotonic saline or isotonic dextrose buffered if necessary to a pH of 5 to 9. Alternatively, the parenteral composition may be one designed for slow release in which case the amount of polypeptide per unit dose is in general greater than that required when a conventional injectable formulation is used. A preferred slow release formulation is a continuous release formulation, for example a formulation of the type described in European Patent Application No. 58481 or, for peptides of formula I containing at least one basic group, a formulation as described in International Patent Application, Publication No. WO93/24150, which patent applications are incorporated herein by reference. Certain peptides of the present invention possess solubility characteristics which make them particularly suitable for the manufacture and processing of slow release parenteral formulations, particularly formulations containing biodegradeable polyesters such as polylactides and for providing slow release formulations with beneficial release profiles. Furthermore, peptides of the present invention containing one or more basic groups, particularly arginine, can also form peptide-polymer salts with acid-ended polyesters, such as polylactides, and such peptides and peptide-polymer salts constitute a further aspect of the present invention. Certain such salts possess solubility characteristics which make them particularly suitable for the manufacture and processing of slow release parenteral formulations, for example as described in WO93/24150, and for providing slow release formulations with beneficial release profiles and storage stability characteristics. A preferred slow release parenteral formulation contains from 1 to 100 mg (such as 5 to 50 mg) of polypeptide per unit dose. A preferred slow release parenteral formulation is also one designed for slow release over a period of at least 5 days.

Preferred peptides of the present invention include those which, when in the form of an extruded polymer depot formulation, show minimal loss due to degradation on extrusion or which show minimal degradation on release from such a depot formulation. Typical procedures for measuring the level of degradation of a peptide of the present invention are as follows:

Prenaration of extruded polymer depot formulation of peptide

About 20 mg of peptide is accurately weighed and sufficient polymer (50/50% molar poly(D,L-lactic acid/glycolic acid) copolymer of approximate weight average molecular weight 20kD and approximate polydispersity of 1.7 as determined by size exclusion chromatography relative to polystyrene standards) added to produce an approximate 20% w/w mixture. This is dissolved in hydride-free glacial acetic acid to produce an approximate 10% w/v solution. The solution is freeze dried and the resulting freeze dried product is stored under vacii, prior to use.

About 100 mg of freeze dried material is loaded into the barrel of a small laboratory extruder and the plunger pushed down to consolidate the sample. The extruder is heated to between 90 and 95° C. and held at this temperature for 10 minutes before the freeze dried material is extruded under presure to give a cylindrical extrudate of approximately 1 mm in diameter.

Analysis of peptide content of extruded polymer depot formulation of peptide

Two approximate 5 mm lengths of extruded polymer depot containing peptide are accurately weogjed amd eacj dosspved 1 ml of anhydride-free glacial acetic acid in separate 25 ml bolumertic flasks. After about 1.5 hours the volume of each is made up to 25 ml with distilled water, causing the polymer to precipitate. The solids are filtered off using a 0.5 µm Millex PTFE filter and the solutions, A, collected.

A series of standard solutions are prepared from a stock solution of peptide in distilled water at 0.5 mg/ml and a stock solution of polymer in anhydride-free glacial acetic acid at 2.5 mg/ml as follows with each solution made up to 10 ml with distilled water:

| Concentration of peptide(µ g/ml) | Volume of stock polymer solution (µl) | Volume of stock peptide solution (µl) |
|---|---|---|
| 50 | 1000 | 1000 |
| 40 | 1000 | 800 |
| 30 | 1000 | 600 |
| 20 | 1000 | 400 |
| 10 | 1000 | 200 |
| 5 | 1000 | 100 |
| 0 | 1000 | 0 |

Each standard is filtered through a 5 µm Millex PTFE filter and an aliquot of filtrate, together with aliquots of the solutions A, analysed by HPLC using duplicate sample injections. The peptide content of the extruded polymer depot formulation of peptide is calculated from the concentration of peptide in solutions A, which is determined by comparing the area of the peptide peak in solutions A with the area of the peptide peak from the standard solutions. Preferred peptides of the present invention show minimal loss due to degradation on extrusion and thus the peptide content of the extruded polymer depot formulation is close to the approximate theoretical value of 20% w/w.

Degradation of Dettide on in vitro release from an extruded polymer depot

A solution of McIlvaine's citric acid-phosphate buffer solution at pH 7.6 containing 0.02% sodium azide, is filtered through a 0.22 µfilter and stored at 4° C. Approximately 10 mg of extruded polymer depot containing peptide is placed in two small vials and 2 ml of the buffer solution added. The vials are then capped and stored in a water bath at 37° C. for a month. At suitable time points over a month, three 0.6ml aliquots of release medium are removed from each vial and either analysed by HPLC or stored frozen in an HPLC vial at −18° C. prior to analysis by HPLC. 1.8 ml of the buffer solution is added to each vial containing the depot to replace the release medium that has been removed at each time point.

The average amount of intact peptide in the release medium at each time point is determined by HPLC using duplicate sample injections by comparing the area of the peptide peak in the release media with the area of the peptide peak from standard buffer solutions of peptide at known concentrations. The approximate average amount of peptide degradation products in the release media at each time point is determined by HPLC by comparing the area of additional new peaks in the release media with the area of the peptide peak from standard buffer solutions of peptide at known concentrations and assuming the extinction coefficient has not changed. The average cumulative in vitro release profile of intact peptide and total peptide (intact peptide and peptide degradation products) is determined from the amounts of intact peptide and peptide degradation products in the release medium at each time point. Preferred peptides of the present invention show minimal degradation on in vitro release and thus show total peptide degradation products of less than 10% and preferably less than 5% of total peptide after a month of in vitro release into Mcllvaine's buffer solution at pH 7.6 at 37° C.

The composition of the invention will generally be administered to man such that, for example, a daily dose will be from 10 micrograms to 5000 mg, preferably 0.1 to 100 mg, for a 70 kg patient, given in divided doses as necessary. The precise amount of composition administered and the route and form of administration may depend on the size, age and sex of the person being treated and on the particular disease or medical condition being treated and its severity, according to principles well know in the medical art.

A peptide derivative of formula I, or a pharmaceutically acceptable salt thereof, may also be advantageously administered for therapeutic or prophylactic purposes together with one or more other pharmacological agents known in the general art to be of value in treating or relieving the symptoms of (or to be a disease modifying agent of) one or more of the diseases or medical conditions referred to hereinabove, such as a NSAID (such as ibuprofen or piroxicam), an analgesic (such as paracetamol), a corticosteroid, a muscle relaxant, a lipoxygenase inhibitor, methotrexate, azathioprine, D-penicillamine, Cyclosporin A or a monoclonal antibody therapy (such as anti-CD4 or anti-TNF). In diabetes the peptide derivative may be co-administered with insulin or other therapies for diabetes or diabetes complications, (such as an aldose reductase inhibitor). It is to be understood that such combination therapy constitutes a further aspect of the invention.

According to a further aspect of the present invention there is provided a method for treating a MHC class II dependent T-cell mediated autoimmune or inflammatory disease, for example one or more of the diseases or medical conditions referred to herein, which comprises administering to a warm-blooded mammal (including man) in need of such treatment an effective amount of a peptide derivative of formula I, or a pharmaceutically acceptable salt thereof. The invention also provides the use of a peptide derivative of formula I or a pharmaceutically acceptable salt thereof, in the production of a novel medicament for use in the treatment of a MHC class If dependent T-cell mediated autoimmune or imflammatory disease.

In addition to their aforesaid use in therapeutic medicine in humans, the peptide derivatives of formula I are also useful in the veterinary treatment of similar conditions affecting commercially valuable warm-blooded animals, such as dogs, cats, horses and cattle.

In general for such treatment, the peptide derivative of the formula I will be administered in an analogous amount and manner to those described above for administration to humans. The peptide derivatives of formula I are also of value as pharmacological tools in the development and standardisation of test systems for the evaluation of the effects of MHC class II molecules in laboratory animals such as cats, dogs, rabbits, monkeys, rats and mice, as part of the continuing search for new and improved therapeutic agents, or as diagnostic reagents.

The invention will now be illustrated by the following non-limiting Examples in which, unless otherwise stated:

(i) concentrations and evaporations were carried out by rotary evaporation in vacuo;

(ii) operations were carried out at room temperature, that is in the range 18–26° C.;

(iii) yields, when given, are intended for the assistance of the reader only and are not necessarily the maximum attainable by diligent process development;

(iv) the following abbreviations are used:
Phv=5-phenylvaleryl; Boc=tert-butoxycarbonyl; tBu=tert-butyl; DMF=N,N-dimethylformamide; HOBT=1-hydroxy-benzotriazole; Met=methionine; Fmoc=9-fluorenylmethyloxycarbonyl; Fmoc-Pip-OH=N-(9-fluorenylmethoxycarbonyl)piperidine4-carboxylic acid; Fmoc-Papa-OH=4-[N-(9-fluorenylmethoxycarbonyl)amino]phenylacetic acid; CbZ=benzyloxycarbonyl; Pmc=2,2,5,7,8-pentamethylchroman-6-sulphonyl; Pbf=2,2,4,6,7-pentamethyldihydrobenzofiuran-5-sulphonyl; THF=tetrahydrofuran; DMSO=dimethylsulfoxide; HBTU=2-(1H-benzotriazol-1yl)-1,1,3,3-tetramethyluroniumhexafluorophosphate; DIPEA=diisopropylethylamine: TFA=trifluoroacetic acid; Su is succinimide attached via the ring nitrogen atom; HPLC=high pressure liquid chromatography; and RP-HPLC=reverse phase high pressure liquid chromatography (which unless otherwise stated was carried out on a Vydac C18 column 218TP54, 4.6×250 mm);

(v) flash chromatography and chromatography on silica were performed on Merck Kieselgel 60 (Art No. 9385) obtained from E Merck, Darmstadt, Germany;

(vi) $^1$H NMR spectra were determined at 200 Mhz in $CDCL_3$ or $d_6$-dimethylsulphoxide ($d_6$-DMSO) using tetramethylsilane (TMS) as an internal standard, and are expressed as chemical shift (delta) values in parts per million relative to TMS using conventional abbreviations for designation of major peaks: s, singlet; m, multiplet, t, triplet; br broad, d, doublet;

(vii) the following Fmoc-protected amino acids were used for the introduction of a Lys, Thr, Arg or His residue: for Lys: Fmoc-Lys(Boc)-OH; for Thr: Fmoc-Thr(OBu)-OH; for Arg: Fmoc-Arg(Pmc)-OH or Fmoc-Arg(Pbf)-OH; and for His: Fmoc-His(Trt)-OH;

(viii) in Example 2, where formula III is referred to this means formula III in which Rb is methyl;

(ix) in Examples 17 and 31, where in the name of the product the term 'morpholine' is used, this means that the morpholine group is attached by the ring nitrogen to the adjacent methylene group;

(x) in Example 18 and 34, where in the name of the product the term '$N(CH_2CH_2)_2N$' is used, this represents a piperazine ring; and (xi) in Example 30, where in the name of the product the term "—Lys(=C(NMe$_2$)$_2$—" is used, this represents the L-amino acid residue —HN—CH[CH$_2$CH$_2$CH$_2$CH$_2$N=C(NMe$_2$)$_2$]—CO—.

EXAMPLE 1

Preparation of Phv-Ala-Ala-Ala-Lys-Val-IIb-Ala-Pip-NH$_2$ (SEQ ID NO:1)

1.1 Synthesis of Boc-(D)-Met-(L)-Ala-OMe

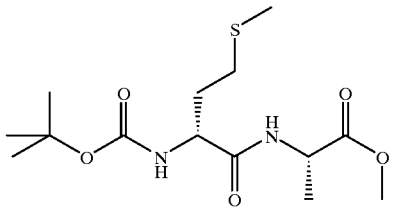

N-methylmorpholine (5.6 g), L-alanine methyl ester hydrochloride (3.9 g), HOBT (4.6 g) and 1-(3-dimethylaminopropyl)-3-ethylcarbodiimide (5.3 g) was added to a solution of Boc-(D)-Methionine (7 g, 0.028 mol) in dry DMF (50 ml). The mixture was stirred overnight. Solvent was removed by evaporation and the residue was partitioned between dichloromethane (100 ml) and 5% aqueous acetic acid (50 ml). On standing HOBT crystallised and was removed by filtration, and the organic layer was separated and washed with aqueous sodium bicarbonate, dried (MgSO$_4$) and evaporated. The residue (8.5 g) was purified by flash chromatography in a sinter funnel eluting with a mixture of dichloromethane and ether (0% to 100% ether). The fractions containing product were combined and evaporated to give Boc-(D)-Met-(L)-Ala-OMe (7.2 g) as a gum which crystallised on standing; NMR (CDCl$_3$): 1.4 (d) 3H), 1.45 (s, 9H), 1.95 (m, 1H), 2.1 (s, 3H), 2.1 (m, 1H), 2.6 (m, 2H), 3.75 (s, 3H), 4.3 (bs, 1H), 4.6 (m, 1H), 5.3 (m, 1H), 6.9 (bs, 1H).

1.2 Synthesis of methyl (2S)-2-[(3R)-3-(N-[tert-butyloxycarbonyl]amino)-2-oxo-pyrrolidin-1-yl]propionate

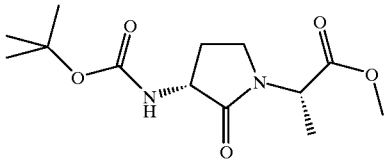

Note: This sequence must be conducted under dry conditions with dry solvents otherwise epimerisation will occur. Methyl iodide (10 ml) was added to Boc-(D)-Met-(L)-Ala-OMe (8 g) in a mixture of DMF (20 ml) and dichloromethane (20 ml) and the mixture was allowed to stand for 16 hours and then evaporated to dryness. Further dichloromethane (2×50 ml) was added and evaporated to remove residual methyl iodide and the residue was dissolved in a mixture of DMF (300 ml) and dichloromethane (300 ml). The mixture was cooled to ~5° C. and sodium Wydride (0.76 g of an 80% dispersion in mineral oil) was add ed in one portion and the mixture was stirred at this temperature for 2 hours. Saturated aqueous ammonium chloride (50 ml) was added and the mixture was evaporated to dryness and then partitioned between water and ether. The ether extract was washed with brine and dried and evaporated to give a gum which was purified by flash chromatography on a sinter flinnel (25% ethyl acetate:hexane to 100% ethylacetate) to give methyl (2S)-2-[(3R)-3-(N-[tert-butyloxycarbonyl]amino)-2-oxo-pyrrolidin-1-yl]propionate as a gum (4.2 g) which crystallised on standing: NMR (CDCl$_3$): 1.4 (s, 9H), 1.4 (d, 3H), 1.8 (m, 1H), 2.6 (m, 1H), 3.4 (m, 2H), 3.7 (m, 3H), 4.2 (m, 1H), 4.9 (q, 1H), 5.2 (bs, 1H).

1.3 Synthesis of (2S)-2-[(3R)-3-(N-[9-fluorenylnmethyloxycarbonyl]amino)-2-oxo-pyrrolidin-1-yl]propionic acid (Fmoc-IIb-OH)

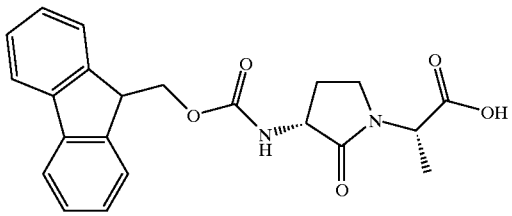

Methyl (2S)-2-m[(3R)-3-(N-[tert-butyloxycarbony]amino)-2-oxo-pyrrolidin-1-yl]propionate (4 g) was refluxed in a mixture of acetone (60 ml), water (40 ml) and concentrated hydrochloric acid (24 ml) for 3 hours and then the mixture was evaporated to dryness. Water was added and the evaporation repeated. The residue was dissolved in water (15 ml) and excess solid sodium bicarbonate was added. 9-Fluorenylmethyl succinimidyl carbonate (5.2 g) in acetone (30 ml) was added. The mixture was stirred for 16 hours and then the solvent was removed by evaporation and the residue was partitioned between water and ether. The aqueous layer was separated, its pH adjusted to ~3 with hydrochloric acid, and extracted with dichioromethane. The organic layer was washed with water, dried (MgSO$_4$) and evaporated to give a white foam which crystallised on trituration with ether to give (2S)-2-[(3R)-3-(N-[9-fluorenylmethyloxycarbonyl]amino)-2-oxo-pyrrolidin-1-yl]propionic acid (4.2 g) as a white solid, mp. 191–3° C. (dec); NMR (CDCl$_3$): 1.4 (d, 3H), 2.0 (m, 1H), 2.6 (m, 1H), 3.4 (m, 2H), 4.2 (t, 1H), 4.4 (m, 3H), 4.9 (m, 1H), 5.8 (bs, 1H), 7.4 (m, 4H), 7.6 (d, 2H), 7.7 (d,2H).

1.4 Synthesis of Phv-Ala-Ala-Ala-Lys-Val-IIb-Ala-Pip-NH$_2$ (SEQ ID NO: 1)

The peptide was prepared by Fmoc solid phase synthesis starting with Fmoc Rink Amide MBHA Resin (Novabiochem, 0.50 g, 0.25 mmoles) in a Bond Elut tube (Varian, 15 ml fitted with a filter in the bottom).

(a) The resin was deprotected using a 20% solution of piperidine in DMF (two treatments with 5 ml for 10 minutes each). After deprotection the resin was thoroughly washed with DMF (5×10 ml).

(b) Acylation was carried out by addition of a solution of Fmoc-Pip-OH (353 mg, 1 mmol), DMF(1.5 ml), HOBT (165 mg, 1 mmol) and diisopropylcarbodiimide (155 microliters, 1 mmol). The coupling was left for approximately 30 minutes, washed with DMF (5×10 ml) and a small portion of the resin checked for completion of acylation using the Kaiser test (E. Kaiser, et al, (1970) Anal. Biochem. 34, 595)

The above deprotection (a) and coupling cycle (b) were repeated using,

Fmoc-Ala-OH (311 mg, 1 mmol);
Fmoc-IIb-OH (394 mg, 1 mmol);
Fmoc-Val-OH (339 mg, 1 mmol);
Fmoc-Lys(Boc)-OH (468 mg, 1 mmol);
Fmoc-Ala-OH (311 mg, 1 mmol);
Fmoc-Ala-OH (311 mg, 1 mmol);
Fmoc-Ala-OH (311 mg, 1 mmol); and
5-Phenylvaleric Acid (178 mg, 1 mmol);

In each case the coupling time was around 30 minutes and a small portion of the resin was checked for completion of acylation by the Kaiser test. The phenylvaleric acid required a double couple to obtain a positive result by the Kaiser test.

The peptide was cleaved from the resin using a mixture of trifluoroacetic acid (7.9 ml) and triethylsilane (0.395 ml). After 2 hours the resin was washed with dichloromethane (approximately 150 ml) and the resulting solution evaporated to dryness. The resulting solid was partitioned between ether (25ml) and water (25 ml) and then the ether was extracted with further portions of water (2×25 ml). The aqueous phases were combined and freeze dried.

The crude product was purified using preparative RP-HPLC (Vydac 218TP1022 column, 250 mm×22 mm), loading the crude material in 5 mls of 20% acetonitrile/water with 200 microliters of DMF. Elution was carried out with a gradient of acetonitrile-water containing 0.1% TFA (15–35% acetonitrile) over 80 minutes at a flow rate of 10 ml/minute. The fractions containing product were combined and freeze dried to give Phv-Ala-Ala-Ala-Lys-Val-IIb-Ala-Pip-NH$_2$ (SEQ ID NO: 1) as a white solid (84 mg; 35% yield).

The product was characterised by HPLC, mass spectroscopy and amino acid analysis.

RP-HPLC Vydac C18 column, 218TP54, 4.6×250 mm, eluting with acetonitrile and water containing 0.1% TFA, using a 10–50% acetonitrile gradient over 30 minutes, flow rate 1.0 ml/minute, indicated 100% purity, retention time 18.56 minutes: mass spectrometry, m/e (positive electrospray (ES+)) 954.6 (MH$^+$); amino acid analysis (acid hydrolysis over 24 hours using a solution of 6N HCl containing 1% phenol at 130° C.) gave (Ala+IIb) 4.80. Val 1.11, Lys 1.07.

Fmoc-Pip-OH was obtained by an analogous method to that described in E. Atherton and R. C. Sheppard ("Solid phase peptide synthesis: a practical approach", IRL press. 1989, page 51) for N-Fmoc-L-methionine:

Fmoc-Pip-OH: NMR (DMSO-d$_6$) 1.3 (m, 2H), 1.7 (m. 2H), 2.5 (m, 2H), 2.9 (t, 2H), 3.7 (m, 1H), 4.2 (t, 1H), 4.4 (d, 2H), 7.4 (m, 4H), 7.7 (d, 2H), 7.9 (d, 2H); mass spectrometry m/e (ES$^+$) 352.2 (MH$^+$)

EXAMPLE 2

Phv-Ala-Ala-Ala-Lys-Val-III-Ala-Pip-NH$_2$ and separation of isomers. (SEQ ID NO: 2)

2.1. Synthesis of (RS)-2-allyl-N-(benzyloxycarbonyl)proline

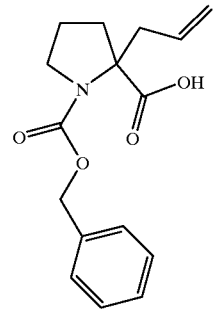

N-benzyloxycarbonylproline methyl ester (13 g) in THF (20 ml) was added dropwise to lithium dilsopropylamide (27.5 ml, 2M in hexane/THF) in THF (100 ml) at −78° C. under nitrogen. The mixture was stirred for 30 minutes and then allyl iodide (5.5 ml) was added dropwise and the mixture stirred for a further 30 minutes and then allowed to warm to ambient temperature. The mixture was then added to aqueous ammonium chloride (200 ml) and extracted with ether (2×200 ml). The ether layer was evaporated and the residue was purified by chromatography on silica using a gradient of hexane increasing to 20% ethyl acetate:hexane. The appropriate fractions, evaporated to dryness, gave methyl (RS)-2-allyl-N-(benzyloxycarbonyl)prolinate (9 g) as an oil.

8.5 g of this material was dissolved in methanol (40 ml) and sodium hydroxide (4.5 g) added in water (20 ml) and the mixture refluxed for 60 minutes. The pH of the mixture was then adjusted to 7 with concentrated hydrochloric acid and the methanol was removed by evaporation. The pH of the mixture was adjusted to 3 and the mixture was extracted with ether (2×50 ml). The combined ether extracts were evaporated to give (RS)-2-allyl-N-(benzyloxycarbonyl) proline as a gum; NMR ($d_6$-DMSO (373 K)): 1.9 (m, 2H), 2.1 (m, 2H), 2.6 (q, 1H), 2.9 (q , 1H), 3.4 (m, 1H), 3.6 (m, 1H), 5.0 (m, 4H), 5.75 (m, 1H), 7.3 (m, 5H)

2.2 Synthesis of [(RS)-2-allyl-N-(benzyloxycarbonyl) prolyl]-(S)-alanine methyl ester

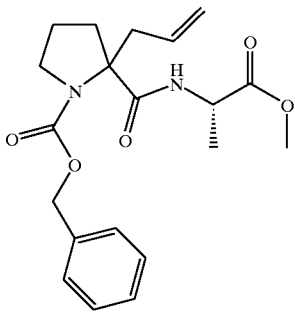

HOBT (7.7 g), N-methylmorpholine (6.6 g), L-alanine methyl ester hydrochloride (4.5 g) and 1-(3-dimethylaminopropyl)-3-ethyl-carbodiimide (5.7 g) was added to (RS)-2-allyl-N-(benzyloxycarbonyl)proline (6.5 g) in DMF (30 ml) and the mixture was stirred for 18 hours and then evaporated. The residue was partitioned between ether and water, filtered to remove HOBt and the organic layer separated. The organic layer was evaporated and the residue was purified by chromatography on silica using a gradient of 20% ethyl acetate in hexane increasing to 50% ethyl acetate in hexane. The appropriate fractions were combined and evaporated to dryness to give [(RS)-2-allyl-N-(benzyloxycarbonyl)prolyl]-(S)-alanine methyl ester (7 g); NMR ($d_6$-DMSO (373 K)): some doubling of peaks due to the mixture of diastereoisomers, 1.25 and 1.3 (2d, 3H), 1.75 (m, 2H), 2.2 (m, 2H), 2.65 (m, 1H), 2.9 (m, 1H), 3.4 (m, 1H), 3.65 (2s, 3H), 3.7 (m, 1H), 4.3 (2q, 1H), 5.0 (m, 4H), 5.7 (m, 1H), 7.3 (m, 5H), 7.4 and 7.5 (bs, 1H).

2.3 Synthesis of methyl (S)-2-(1-benzyloxycarbonyl-6-oxo-1,7-diazaspiro[4.4]non-7-yl)propionate. (CbZIII-OMe)

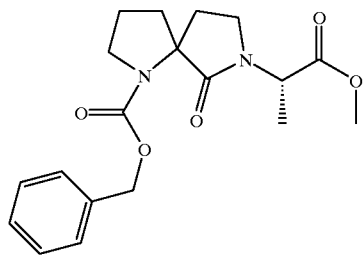

Osmium tetroxide (1.5 ml of 4% aqueous solution) was added to [(RS)-2-allyl-N-(benzyloxycarbonyl)prolyl]-(S)-alanine methyl ester (1.45 g) in a mixture of methanol (30 ml) and water (20 ml). The mixture was stirred under argon for 10 minutes and then sodium periodate (2.45 g) was added in portions. The mixture was stirred for 2 hours and then water (100 ml) was added and the mixture was extracted with ethyl acetate (2×70 ml). The combined extracts were dried and evaporated to give 1.4 g of a gum. The gum was dissolved in dichloromethane (30 ml) and triethylsilane (0.65 g) and then trifluoroacetic acid (4 g) were added dropwise. The mixture was stirred for 3 hours, evaporated and the residue partitioned between aqueous sodium bicarbonate and ether. The ether extract was separated and evaporated to dryness. The residue was purified by chromatography on silica using a gradient of 25% ethyl acetate in hekane increasing to 100% ethyl acetate. The appropriate fractions were combined and evaporated to dryness to give methyl (S)-2-(1-benzyloxycarbonyl-6-oxo-1,7-diazaspiro [4.4]non-7-yl)propionate (0.8 g); NMR ($d_6$-DMSO (373 K)): some doubling of peaks due to the mixture of diastereoisomers, 1.25 and 1.35 (2d, 3H), 1.95 (m, 6H), 3.1–3.5 (m, 4H), 3.6 and 3.65 (2s, 3H), 4.5 and 4.65 (2q, 1H), 5.05 (m, 2H), 7.25 (m, 5H).

2.4 Synthesis of (S)-2-(6-oxo-1,7-diazaspiro[4.4]non-7-yl) propionic acid (H-III-OH)

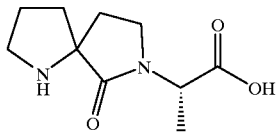

Potassium carbonate (2.5 g) was added to methyl (S)-2-(1-benzyloxycarbonyl-6-oxo-1,7-diazaspiro[4.4]non-7-yl) propionate (3.3 g) in a mixture of methanol (40 ml) and water (40 ml) and the mixture was stirred at ambient temperature for 10 hours. The pH was adjusted to ~5 with concentrated hydrochloric acid and the mixture was evaporated to dryness. The residue was dissolved in water (40 ml) and the pH adjusted to 3 with concentrated hydrochloric acid. The mixture was then extracted with dichloromethane (2×50 ml). The combined extracts were dried (MgSO$_4$) and evaporated to yield a foam (2.8 g). The foam was dissolved in methanol (20 ml) and cyclohexene (0.7 g) was added followed by 10% Pd/C (0.5 g). The mixture was refluxed for 2 hours, cooled, filtered and the filtrate was evaporated to give (S)-2-(6-oxo-1,7-diazaspiro[4.4]non-7-yl)propionic acid as a foam (1.9 g); NMR ($d_6$-DMSO): some doubling of peaks due to the mixture of diastereoisomers, 1.25 and 1.3 (2s, 3H), 1.8 (m, 4H), 2.0 (m, 2H), 3.0 (m, 2H), 3.3 (m, 2H), 4.5 (m, 1H).

2.5 Synthesis of (S)-2-[1-(9-fluorenylmethyloxycarbonyl)-6-oxo- 1,7-diazaspiro-[4.4]non-7-yl]propionic acid (Fmoc-III-OH)

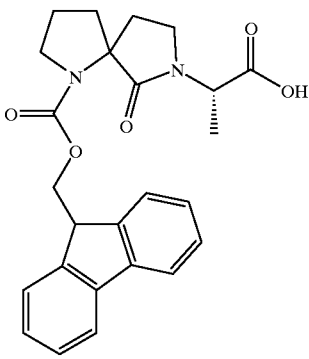

Excess solid sodium bicarbonate was added to (S)-2-(6-oxo-1,7-diazaspiro[4.4]non-7-yl)propionic acid (0.42 g) in water (2 ml) and then 9-fluorenylmethyl succinimidyl carbonate (0.7 g) in acetone (3 ml) was added. The mixture was stirred for 18 hours. The mixture was then added to water (10 ml), extracted with ether (10 ml) and the aqueous layer separated. (The ether extracts were discarded). The pH of the aqueous layer was adjusted to ~3 with concentrated hydrochloric acid and then it was extracted with dichloromethane (2×10 ml). The combined extracts were separated, dried (MgSO$_4$) and evaporated to give (S)-2-[1-(9-fluorenylmethyloxycarbonyl)-6-oxo-1,7-diazaspiro[4.4]non-7-yl]propionic acid (0.62 g) as a white foam; NMR (d$_6$-DMSO (373 K)): some doubling of peaks due to the mixture of diastereoisomers, 1.3 (2d, 3H), 1.6–2.0 (m, 6H), 3.05 (m, 1H), 3.2–3.45 (m, 3H), 4.2–4.4 (m, 1H), 4.5 (m, 1H), 6.2 (s, 2H), 7.35 (m, 4H), 7.8 (m, 4H).

2.6 Synthesis of Phv-Ala-Ala-Ala-Lys-Val-III-Ala-Pip-NH$_2$ and separation of isomers. (SEQ ID NO: 2)

The first part of the synthesis was performed using similar methodology to that described for Example 1.4, but using Fmoc-III-OH in place of Fmoc-IIb-OH. In this case the acylations were performed by activation of the acids in the following way: Acid (1 mmol), HBTU (1 mmol), diisopropylethylamine (2 mmol), DMF (4 ml). All couplings were seen to be complete by the Kaiser test after less than 45 minutes. This methodology was used to give Fmoc-Val-III-Ala-Pip-NH-Resin. The peptide resin was then transferred to an ABI 431 automated peptide synthesiser where the remaining residues in the sequence were coupled following the manufacturer's recommended conditions for single acylations incorporating HBTU/HOBT chemistry, as follows. After deprotection, the resin was washed with DMF (10× 10–20 ml). The carboxylic acid (1 mmol) was activated with HBTU (1 equivalent). HOBT (1 equivalent) and DIPEA (2 equivalents) in DMF for approximately 11 minutes before transfer to the resin. The acylation was carried out for approximately 60 minutes and then the resin was washed with DMF (10×10–20 ml). Fmoc deprotection at each stage was carried out using a 20% solution of piperidine in DMF (two treatments with 5 ml for 10 minutes each). After each deprotection, the resin was thoroughly washed with DMF (5×10 ml).

The peptide was cleaved from the resin by treatment with a mixture of trifluoroacetic acid (TFA), triethylsilane (TES) and water (10 ml, 90:5:5) for 1.5 hours. The resin was filtered off, washed thoroughly with TFA, the collected filtrate concentrated to dryness by rotary evaporation and then the resulting residue triturated with ether to yield Phv-Ala-Ala-Ala-Lys-Val-III-Ala-Pip-NH$_2$ (SEQ ID NO: 2) containing two major components (RP-HPLC (Vydac 218TP54 C18 column) indicated a 52:48 mixture). The more polar diastereomer eluted with a retention time of 12.5 minutes and the less polar diastereomer with a retention time of 16.5 minutes using an acetonitrile:water (containing 0.1% TFA) gradient of 20–50% over 20 minutes at a flow rate of 1 ml/minute. The peptide was further purified by preparative RP-HPLC, essentially as described for Example 1.4, to give the two isolated components, both >95% pure by RP-HPLC. The more polar diastereomer was more potent than the less polar diastereomer in Tests A and B and was cbaracterised as follows:

RP-HPLC (20–50% acetonitrile gradient over 20 minutes, flow rate 1 ml/minute) retention time=12.3 minutes; mass spectrometry, m/e (ES+) 994.5 (MH$^+$); amino acid analysis gave Ala 3.99, Lys 1.20, Val 0.73.

EXAMPLE 3

Phv-Ala-Lys-Ala-IIb-Ala-Ala-Ala-Pip-NH$_2$ (SEQ ID NO: 3)

The synthesis was performed manually, and the purification carried out using similar methodology to that described for Example 1.4, coupling and deprotecting the Fmoc-protected amino acids and Fmoc-IIb-OH in the appropriate order. The product was characterised by HPLC, mass spectroscopy and amino acid analysis in a similar manner to that described for Example 1.4; RP-HPLC (eluting with acetonitrile and water containing 0.1% TFA, using a 25–40% acetonitrile gradient over 20 minutes, flow rate 1.0 ml/minute) retention time= 5.56 minutes; mass spectrometry, m/e (ES+) 926.5 (MH$^+$) amino acid analysis gave (Ala+IIb) 5.87, Lys 1.12.

EXAMPLE 4

Phv-Ile-Ala-Ala-Arg-Thr-IIb-Ala-Papa-NH$_2$ (SEQ ID NO: 4)

The synthesis was performed manually, and the purification carried out, using similar methodology to that described for Example 1.4, coupling and deprotecting the Fmoc-Papa-OH (used instead of Fmoc-Pip-OH), Fmoc-protected amino acids and Fmoc-IIb-OH in the appropriate order. The product was characterised by HPLC, mass spectroscopy and amino acid analysis in a similar manner to that described for Example 1.4; RP-HPLC (eluting with acetonitrile and water containing 0.1% TFA, using a 20–50% acetonitrile gradient over 30 minutes, flow rate 1.0 ml/minute) retention time= 17.08minutes; mass spectrometry, m/e (ES+) 1048.7 (MH$^+$); amino acid analysis gave Arg 0.98, Ala 3.00, IIb 1.27, Thr 0.86, Ile 0.88.

Fmoc-Papa-OH was obtained by an analogous method to that described in E. Atherton and R. C. Sheppard ("Solid phase peptide synthesis: a practical approach", IRL press, 1989, page 51) for N-Fmoc-L-methionine:

Fmoc-Papa-OH: NMR (DMSO-d$_6$) 3.5 (s, 2H), 4.25 (to 1H), 4.5 (d, 2H), 7.1 (d, 2H), 7.4 (m, 6H), 7.75 (d, 2H), 7.9 (d, 2H), 9.6 (s, 1H); mass spectrometry m/e (ES)$^-$372.1 (M-H)$^-$

EXAMPLE 5

Phv-Arg-Ala-Ala-Ala-Val-IIb-Ala-Pip-NH$_2$ (SEQ ID NO: 5)

The synthesis was performed manually using similar methodology to that described for Example 1.4, coupling and deprotecting the Fmoc-protected amino acids and Fmoc-IIb-OH in the appropriate order. The product was purified using preparative RP-HPLC in a similar manner to that described for Example 1.4, eluting with a gradient of acetonitrile-water containing 0.1% TFA (15–40% acetonitrile) over 60 minutes at a flow rate of 10 ml/minute. The product was characterised by HPLC, mass spectroscopy and amino acid analysis in a similar manner to that described for Example 1.4;

RP-HPLC (eluting with acetonitrile and water containing 0.1% TFA, using a 10–50% acetonitrile gradient over 30 minutes, flow rate 1.0 ml/minute) retention time=18.28 minutes; mass spectrometry, m/e (ES+) 982.5 (MH⁺); amino acid analysis gave Arg 1.12, (Ala+IIb) 3.8, Val 1.12.

EXAMPLE 6

Phv-Arg-Ala-Ala-Ala-Thr-IIb-Ala-Papa-NH$_2$ (SEQ ID NO: 6)

The first part of the synthesis was performed manually, using similar methodology to that described for Example 1.4, coupling and deprotecting the Fmoc-Papa-OH (used instead of Fmoc-Pip-OH), Fmoc-protected amino acids and Fmoc-IIb-OH in the appropriate order to give Fmoc-Thr(OBu)-IIb-Ala-Papa-NH-resin. The peptide resin was then transferred to an automated synthesiser (ACT 357) and the remaining residues were coupled following the manufacturer's recommended conditions for single acylations incorporating HBTU/HOBT chemistry. The peptide was cleaved from the resin and purified by preparative RP-HPLC using a similar procedure to that described in Example 1.4. The peptide was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.0 ml/minute) retention time=18.21minutes; mass spectrometry, m/e (ES+) 1006.4 (MH⁺); amino acid analysis gave Arg 1.10, Ala 3.88, IIb 1.04, Thr 0.95.

EXAMPLE 7

Phv-Ala-Ala-Ala-Arg-Val-IIb-Ala-Papa-NH$_2$ (SEQ ID NO: 7)

The first part of the synthesis was performed manually, using similar methodology to that described for Example 1.4, coupling and deprotecting the Fmoc-Papa-OH (used instead of Fmoc-Pip-OH), Fmoc-protected amino acids and Fmoc-IIb-OH in the appropriate order to give Fmoc-Val-IIb-Ala-Papa-NH-resin. The peptide resin was then transferred to an automated synthesiser (ABI 431 ) and the remaining residues coupled following the manufacturer's recommended conditions for single acylations incorporating HBTU/HOBT chemistry. The peptide was cleaved from the resin and purified by preparative RP-HPLC using a similar procedure to that described in Example 2.6. The peptide was characterised by RPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.1 ml/minute) retention time=20.87 minutes; mass spectrometry, mnie (ES+) 1004.6 (MH⁺); amino acid analysis gave Arg 0.96, (Ala+IIb) 5.05, Val 0.97.

EXAMPLE 8

Phv-Ala-Arg-Ala-Arg-Val-IIb-Gly-Papa-NH$_2$ (SEQ ID NO: 8)

The first part of the synthesis was performed manually, using similar methodology to that described for Example 1.4, coupling and deprotecting Fmoc-Papa-OH (used instead of Fmoc-Pip-OH), the Fmoc-protected amino acids and Fmoc-IIb-OH, to give Fmoc-Val-IIb-Gly-Papa-NH-resin. The peptide resin was then transferred to an automated synthesiser (ABI 431 ) and the remaining residues coupled following the manufacturer's recommended conditions for single acylations incorporating HBTU/HOBT chemistry. The peptide was cleaved from the resin and purified by preparative RP-HPLC using a similar procedure to that described in Example 2.6. The peptide was characterised by HPLC, mass spectscopy and amino acid analysis in a similar manner to that described for Example 1.4; RP-HPLC (eluting with acetonitrile and water containing 0.1% TFA, using a 10–50% acetonitrile gradient over 30 minutes, flow rate 10 ml/minute) retention time=18.12 minutes; mass spectrometry, m/e (ES+) 538.4 (M+2H⁺⁺); amino acid analysis gave Arg 0.92, Ala 2.16, (Gly+IIb) 2.12, Val 0.88.

EXAMPLE 9

Phv-Ala-lle-Ain-Arg-Val-IIb-Ala-Pip-NH$_2$ (SEQ ID NO: 9)

The synthesis was performed manually, and the purification carried out, using similar methodology to that described for Example 1.4, coupling and deprotecting the Fmoc-protected amino acids and Fmoc-IIb-OH in the appropriate order. The product was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.0 ml/minute) retention time= 23.4 minutes; mass spectrometry, mn/e (ES+) 1024.6 (MH⁺); amino acid analysis gave Arg 1.15, (Ala+IIb) 3.88, Val 0.96, Ile 1.02.

EXAMPLE 10

Phv-Ala-Arg-Ala-His-Val-IIb-Ala-Papa-NH$_2$ (SEQ ID NO: 10)

The first part of the synthesis was performed manually, using similar methodology to that described for Example 1.4, coupling and deprotecting the Fmoc-Papa-OH (used instead of Fmoc-Pip-OH), Fmoc-protected amino acids and Fmoc-IIb-OH in the appropriate order to give Fmoc-Val-IIb-Ala-Papa-NH-resin. The peptide resin was then transferred to an automated synthesiser (ABI 431) and the remaining residues coupled following the manufacturer's recommended conditions for single acylations incorporating HBTU/HOBT chemistry. The peptide was cleaved from the resin and purified by preparative RP-HPLC using a similar procedure to that described in Example 2.6. The peptide was characterised by HPLC, mass spectroscopy and amino acid analysis in a similar manner to that described for Example 1.4; RP-HPLC (eluting with acetonitrile and water containing 0.1% TFA, using a 20–50% acetonitrile gradient over 30 minutes, flow rate 1.0 ml/minute) retention time=18.8 minutes; mass spectrometry, mile (ES+) 1070.6 (MH⁺); amino acid analysis gave Arg 1.02, (Ala+IIb) 4.12, Val 0.90, His 0.95.

EXAMPLE 11

Phv-Ala-Ala-Asn-Arg-Val-IIb-Ala-Pip-NH$_2$ (SEQ ID NO: 11)

The first part of the synthesis was performed manually, using similar methodology to that described for Example 1.4, coupling and deprotecting the Fmoc-protected amino acids and Fmoc-IIb-OH in the appropriate order, to give Fmoc-IIb-Ala-Pip-NH-resin. The peptide resin was then transferred to an automated synthesiser (ABI 431) and the remaining residues coupled following the manufacturer's recommended conditions for single acylations incorporating HBTU/HOBT chemistry. The peptide was cleaved from the resin and purified by preparative RP-HPLC using a similar procedure to that described in Example 2.6. The peptide was characterised by HPLC, mass spectroscopy and amino acid analvsis in a similar manner to that described for Example 1.4; RP-HPLC (eluting with acetonitrile and water containing 0.1% TFA, using a 10–50% acetonitrile gradient over 30 minutes flow rate 1.0 ml/minute) retention time=17.66 minutes; mass spectrometry, mn/e (ES+) 1025.5 (MH$^+$); amino acid analysis gave Arg 1.04, Ala 2.94, Val 0.95, Asp 1.05.

EXAMPLE 12

Phv-Ala-Arg-Ala-IIb-Ala-Ala-Ala-Pip-NH$_2$ (SEQ ID NO: 12)

The first part of the synthesis was carried out automatically on an ABI 431 automated synthesiser using similar methodology to that described in Example 2.6, coupling the Fmoc-protected amino acids in the appropriate order, to give Fmoc-Ala-Ala-Pip-NH-Resin. The remainder of the synthesis was performed manually, and the product purified by preparative RP-HPLC, using a similar procedure to that described in Example 1.4. The peptide was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.0 ml/minute) retention time=16.68 minutes; mass spectrometry, m/e (ES+) 954.6 (MH$^+$); amino acid analysis gave Arg 1.09, (Ala+IIb) 5.88.

EXAMPLE 13

Phv-Ala-Arg-Ala-Ala-Thr-IIb-Gly-NH(CH$_2$)$_3$NH.C(=NH).NH$_2$ (SEQ ID NO: 14)

(a) Preparation of Phv-Ala-Arg-Ala-Ala-Thr-IIb-Gly-NH(CH$_2$)$_3$NH$_2$ (SEQ ID NO: 13)

2-Chlorotrityl chloride resin, (0.4 g ca. 0.25 mmole of available chlorine) was converted to (3-aminopropyl)aminoresin by reaction with 1.3-diaminopropane (0.42 ml) in DMF (4 ml) for 1 hour at ambient temperature. After thorough washing with DMF, the resin was transferred to an Applied Biosystems 430A peptide synthesiser and the sequential coupling and deprotection of the appropriate protected amino acids was carried out following the manufacturer's recommended conditions. The resin was then washed with methanol and dried (0.722 g). The peptide was cleaved from the resin and purified by preparative RP-HPLC using a similar procedure to that described in Example 2.6. The product was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 40 minutes, flow rate 1.2 ml/minute) retention time=17.76 minutes. There was thus obtained Phv-Ala-Arg-Ala-Ala-Thr-IIb-Gly-NH(CH$_2$)$_3$NH$_2$ (SEQ ID NO: 13) (329 mg after freeze drying); mass spectrometry, m/e (ES$^+$) 916.5 (MH$^+$).

(b) Preparation of Phv-Ala-Arg-Ala-Ala-Thr-IIb-Gly-NH(CH$_2$)$_3$NH.C(=NH).NH$_2$ (SEQ ID NO: 14)
Phv-Ala-Arg-Ala-Ala-Thr-IIb-Gly-NH(CH$_2$)$_3$NH$_2$ (SEQ ID NO: 13) (329 mg) was dissolved in a mixture of water (5 ml) and acetonitrile (5 ml) and 1-H-pyrazole-1-carboxamidine hydrochloride (132 mg, 3 equivalents) and diisopropylethylamine (52 microliters, 1 equivalent) were added. The mixture was stirred at ambient temperature for 4 days. The mixture was purified by preparative RP-HPLC and characterised by HPLC, mass spectroscopy and amino acid analysis in a similar manner to that described for Example 1.4. There was thus obtained Phv-Ala-Arg-Ala-Ala-Thr-IIb-Gly-NH(CH$_2$)$_3$NH.C(=NH).NH$_2$ (SEQ ID NO: 14) (178 mg); RP-HPLC (eluting with acetonitrile and water containing 0.1% TFA, using a 10–50% acetonitrile gradient over 40 minutes, flow rate 1.2 ml/minute) retention time=18.42 minutes; mass spectrometry, m/e (ES$^+$) 958.5 (MH$^+$); amino acid analysis gave Thr 0.86, Gly 0.90; Ala 3.20, Arg 1.00

EXAMPLE 14

Phv-Ala-Arg-Ala-Arg-Thr-IIb-Gly-NHEt (SEQ ID NO: 15)

The first part of the synthesis was carried out on an Applied Biosystems 430A synthesiser and the sequential coupling and deprotection of the appropriate protected amino acids was carried out following the manufacturer's recommended conditions, starting from Boc-Gly-O-Benzyl ester resin (Merrifield resin) (0.54 g, 0.25 mmole). The resin was washed with methanol and dnred (871 mg) and then stirred gently with DMF (10 ml) and 2M ethylamine in methanol (10 ml) at ambient temperature for 7 days. RP-HPLC indicated a rapid release of methyl ester into solution followed by a slow conversion to the slightly more hydrophilic N-ethylamide. The mixture was filtered and the resin was washed with DMF. Evaporation of the solvents afforded the crude, protected peptide as the N-ethylamide. The peptide was deprotected using a mixture of TFA, TES and water (90:5:5) and purified by preparative RP-HPLC using a similar procedure to that described in Example 2.6 to give Phv-Ala-Arg-Ala-Arg-Thr-IIb-Gly-NHEt (SEQ ID NO: 15) (168 mg). The peptide was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 40 min, flow rate 1.2 ml/minute) retention time=17.85 minutes; mass spectroscopy, m/e (ES$^+$) 972.5 (MH$^+$); amino acid analysis gave Thr 0.83, Gly 1.03, Ala 2.17. IIb 0.9, Arg 2.00.

EXAMPLE 15 and 16

Phv-Gap-Ala-Ala-Ala-Thr-IIb-Ala-Papa-NH$_2$ (Example 15) (SEQ ID NO: 16)

Phv-Gap(Me)$_4$-Ala-Ala-Ala-Thr-IIb-Ala-Papa-NH$_2$ (Example 16) (SEQ ID NO: 17)

(a) Preparation of Phv-Dap-Ala-Ala-Ala-Thr-IIb-Ala-Papa-NH$_2$ (SEQ ID NO: 36) (Dap or 2,3-diaminoproprionic acid is referred to as "Dpr" in the sequence listing).

The synthesis was performed automatically on an Applied Biosystems 430A synthesiser, using Fmoc Rink Amide resin (0.25 mmole), and the sequential coupling and deprotection of the appropriate protected amino acids was carried out following the manufacturer's recommended conditions. The Dap residue was incorporated by using Fmoc-Dap(Boc)-OH at the appropriate stage in the synthesis. The completed resin was dried. Yield 1.292 g (weight gain, 792 mg). The peptide was cleaved from the resin and purified by preparative RP-HPLC using a similar procedure to that described in Example 1.4, but using a Dynamax 60A column (one inch internal diameter) eluting with acetonitrile and water containing 0.1% TFA (gradient 10–40% acetonitrile) over 60 minutes at a flow rate of 12 ml/minute, to give Phv-Dap-Ala-Ala-Ala-Thr-IIb-Ala-Papa-NH$_2$ (SEQ ID NO: 36) (304 mg). The peptide was charactenrsed by HPLC and mass spectroscopy in a similar manner to that described for Example 1.4; RP-HPLC (eluting with acetonitrile and water containing 0.1% TFA, using a 10–40% acetonitrile gradient over 40 min, flow rate 1.2 ml/minute) retention time=24.5 minutes; mass spectroscopy, m/e (ES$^+$) 937.1 (MH$^+$).

(b) The Dap peptide from (a) was dissolved in water (7 ml) and acetonitrile (8 ml) and treated with 1-H-pyrazole-1-carboxyamidine hydrochloride (130 mg) and diisopropylethyl amine (53 microliters) at ambient temperature for 1 week. RP-HPLC indicated only 40% conversion to the corresponding Gap peptide. Attempted preparative RP-HPLC failed to completely separate the two compounds. Accordingly, the mixture was treated with HBTU (87 mg) and dilsopropylethylamine (50 microliters) in DMF (50 ml) for 16 hours to convert the unchanged Dap peptide to the tetramethylguanidine (GapMe$_4$) peptide. The extra hydrophobicity of this compound enabled an easier preparative HPLC (conditions as described in (a)), which was carried out using identical conditions to those described in (a) above, to give both (i) Phv-Gap-Ala-Ala-Ala-Thr-IIb-Ala-Papa-NH$_2$ (SEQ ID NO: 16) (80 mg) which was characterised by HPLC, mass spectroscopy, and amino acid analysis in a similar manner to that described in Example 1.4; RP-HPLC (10–40% acetonitrile gradient over 40 min, flow rate 1.2 ml/minute) retention time=26.2 minutes; mass spectroscopy, m/e (ES$^+$) 978.5 (MH$^+$); amino acid analysis gave Thr 0.90, Ala 4.05, IIb present, peak in Trp position for Gap. and (ii) Phv-Gap(Me)$_4$-Ala-Ala-Ala-Thr-IIb-Ala-Papa-NH$_2$ (122 mg) (SEQ ID NO: 17), which was characterised as for (i) above; RP-HPLC (eluant and gradient as in (i) above) retention time=28.4 minutes; mass spectroscopy, m/e (ES$^+$) 1034.6 (MH$^+$); amino acid analysis gave Thr 0.90, Ala 4.11. IIb present, peak in Trp position for Gap(Me)$_4$.

EXAMPLE 17

Phv-Arg-AIa-AIa-AIa-Thr-IIb-Gly-NHCH$_2$CH$_2$-Morpholine (SEQ ID NO: 18)

A protected fragment strategy was adopted. Fmoc-Gly-O-Chlorotrityl resin (1 mmol, 1 g) was prepared automatically on an Applied Biosystems 430A synthesiser by coupling Fmoc-Gly-OH (2 mmol) with 2-chlorotritylchloride resin (1 g, 1 mmol) in DMF (10 ml) in the presence of N-diisopropylethylamine (4 mmol) and elongated by a double coupling strategy (in a similar manner to that described in Example 2.6) to give the protected peptide resin (2.15 g). After cleavage from the resin with dichloromethane (30 ml), acetic acid (5 ml) and trifluoroethanol (5 ml) at ambient temperature for 1 hour, the resin was filtered off and washed with dichloromethane and acetic acid. Evaporation of the solvents and subsequent freeze-drying from aqueous acetonitrile afforded the required protected peptide acid (1.23 g). The peptide was characterised in a similar manner to that described in Example 1.4; RP-HPLC (20–80% acetonitrile gradient over 40 minutes, flow rate 1.2 ml/minute) retention time=26.2 minutes.

The protected acid (235 mg, 0.2 mmol) was coupled to 4-(2-aminoethyl)morpholine (27 microliters, 1 equivalent) in DMF (10 ml) with HBTU (76 mg, 1 equivalent) and diisopropylethylamine (70 microliters). Evaporation of the solvent, deprotection with 90% TFA/H$_2$O and purification, using a similar procedure to that described in Example 1.4, afforded the pure amide (150 mg). The peptide was characterised by HPLC, mass spectroscopy and amino acid analysis in a similar manner to that described for Example 1.4; RP-HPLC (10–40% acetonitrile gradient over 40 minutes, flow 1.2 ml/minute) retention time=18.6 minutes; mass spectroscopy, m/e (ES$^+$) 972.8 (MH$^+$); amino acid analysis gave Thr 0.6, Gly 1.02, Ala 2.94, IIb 0.9, Arg 1.00.

EXAMPLE 18

Phv-Arg-Ala-Ala-Ala-Thr-IIb-Gly-N(CH$_2$CH$_2$)$_2$NCH$_2$CH$_2$O-CH$_2$CH$_2$OH (SEQ ID NO: 19)

Using an analogous procedure to that described in Example 17, but using 4-[2-(2-hydroxyethoxy)ethyl]piperazine in place of 4-(2-aminoethyl)morpholine, there was thus obtained Phv-Arg-Ala-Ala-Ala-Thr-IIb-Gly-N(CH$_2$CH$_2$)$_2$NCH$_2$CH$_2$O-CH$_2$CH$_2$OH (SEQ ID NO: 19). The peptide was characterised by HPLC, mass spectroscopy and amino acid analysis in a similar manner to that described for Example 1.4; RP-HPLC (using an eluant and gradient as used in Example 17) retention time=20.5 minutes; mass spectroscopy, m/e (ES$^+$) 1016.8 (MH$^+$); amino acid analysis gave Thr 0.89, Gly 1.02, Ala 2.98, IIb 1.05, Arg 1.00.

EXAMPLE 19

Phv-Arg-Ala-Ala-Ala-Thr-Ib-Gly-Pape-NHC(=NH)NH$_2$ (SEQ ID NO: 20)

Using an analogous procedure to that described in Example 17, but using 4-(2-guanidinoethyl)aniline in place of 4-(2-aminoethyl)morpholine, there was thus obtained Phv-Arg-Ala-Ala-Ala-Thr-IIb-Gly-Pape-NHC(=NH)NH$_2$ (SEQ ID NO: 20). The peptide was purified by preparative HPLC in a similar manner to that described for Example 1.4, but using a Vydac 201HS1022 column (one inch internal diameter) and eluting with a gradient of acetonitrile-water containing 0.1% TFA (10–35% acetonitrile) over 60 minutes at a flow rate of 12 ml/minute. The peptide was characterised by HPLC mass spectroscopy and amino acid analysis; RP-HPLC (using an eluant and gradient as used in Example 17) retention time=24.2 minutes; mass spectroscopy, m/e (ES$^+$) 1021.1 (MH$^+$): Amino acid analysis gave Thr 0.8, Gly 0.95, Ala 2.86. Arg 1.00, IIb present.

4-(2-Guanidinoethyl)aniline dihydrochloride was prepared as follows. 4—Nitrophenethylamine hydrochloride (1.013 g, 5 mmol), 1H-pyrazole-1-carboxamidine hydrochloride (0.733 g, 5 mmol) and N-diisopropylethylamine (0.88 ml, 5 mmol) in acetonitrile (10 ml) and water (10 ml) were stirred at ambient temperature for 16 hours. Preparative RP-HPLC was carried out in two portions using a Dynamax 60A, C18 column (one inch internal diameter) eluting with acetonitrile and water containing 0.1% TFA to afford pure 4-nitrophenethylguanidine. The product was dissolved in water (10 ml) and one drop of concentrated hydrochloric acid was added, followed by 5% palladium on carbon (100 mg) and hydrogen was bubbled through the solution for 4 hours. The catalyst was removed by filtration and washed with water. Volatile material was removed by evaporation to give 4-(2-guanidinoethyl)aniline dihydrochloride as a brown foam (0.984 g) (after drying over potassium hydroxide pellets).

EXAMPLE 20

Phv-Ala-Ala-Ala-Arg-Thr-IIb-Ala-Papa-NH$_2$ (SEQ ID NO: 21)

The first part of the synthesis was performed manually, using similar methodology to that described for Example 2.6, using HBTU/DIPEA activation and coupling and deprotecting the Fmoc-protected amino acids and Fmoc-IIb-OH in the appropriate order, to give Fmoc-IIb-Ala-Papa-NH-resin.

The peptide resin was then transferred to an automated synthesiser (ABI 431) and the remaining residues coupled following the manufacturer's recommended conditions for single acylations incorporating HBTU/HOBT chemistry. The peptide was cleaved from the resin and purified using a similar procedure to that described in Example 2.6. The peptide was characterised by HPLC, mass spectroscopy and amino acid analysis in a similar manner to that described for Example 1.4; RP-HPLC (eluting with acetonitrile and water containing 0.1% TFA, using a 20–40% acetonitrile gradient over 20 minutes, flow rate 1.0 ml/minute) retention time=11.57 minutes; mass Spectrometry, m/e (ES+) 1006.4 (MH$^+$), 503.8 (M+2H$^{++}$), 514.8 (M+H$^+$+Na$^+$); amino acid analysis gave: Ala 4.19, Arg 0.91, Thr 0.74.

EXAMPLE 21

Phv-Ala-Arg-Ala-Arg-Thr-IIb-Azgly-Papa-NH$_2$ (SEQ ID NO: 22)

The first part of the synthesis was performed manually using similar methodology to that described for Example 2.6, using HBTU/DIPEA activation and coupling and deprotecting the Fmoc-protected amino acids and Fmoc-IIb-OH in the appropriate order, except for incorporation of the Azgly residue. The Azgly residue was incorporated by coupling with Fmoc-Azgly-OSu (obtained as described in EP 518655) (4 equivalents) with HOBT (0.25 equivalents) in DMF at at 50° C. for 4 hours. There was thus obtained Fmoc-IIb-AzGly-Papa-NH-resin. The peptide resin was then transferred to an automated synthesiser (ABI 431) and the remaining residues coupled following the manufacturer's recommended conditions for single acylations incorporating HBTU/HOBT chemistry. The peptide was cleaved from the resin and purified using a similar procedure to that described in Example 2.6. The peptide was characterised by HPLC, mass spectroscopy and amino acid analysis in a similar manner to that described for Example 1.4; RP-HPLC (eluting with acetonitrile and water containing 0.1% TFA, using a 15–35% acetonitrile gradient over 20 minutes, flow rate 1.0 ml/minute) retention time=8.10 minutes; mass Spectrometry, m/e (negative electrospray (ES−)) 1076.4 (MH$^-$); amino acid analysis gave Ala 2.10, Arg 2.00, Thr 0.99.

EXAMPLE 22

Phv-Ala-Arg-Ala-Arg-Thr-IIb-Azgly-NH$_2$ (SEQ ID NO: 23)

An analogous procedure to that described in Example 21 was used. The first part of the synthesis was performed manually using HBTU/DIPEA activation, to give Fmoc-IIb-Azgly-NH-resin. The peptide resin was then transferred to an automated synthesiser (ABI 430A) and the remaining residues coupled following the manufacturer's recommended conditions for single acylations incorporating HBTU/HOBT chemistry. The peptide was cleaved from the resin and purified by preparative RP-HPLC, using a similar procedure to that described in Example 2.6. The peptide was characterised by HPLC, mass spectroscopy and amino acid analysis in a similar manner to that described for Example 1.4; RP-HPLC (eluting with acetonitrile and water containing 0.1% TFA, using a 20–35% acetonitrile gradient over 20 minutes, flow rate 1.0 ml/minute.) retention time=7.26 minutes; mass spectrometry, m/e (ES+) 945.6 (MH$^+$), 473.4 (M+2H$^{++}$); amino acid analysis gave Ala 2.08, Arg 2.00, Thr 0.78.

EXAMPLE 23

Phv-Ala-Arg-Ala-IIb-Ala-Arg-Ala-Papa-NH$_2$ (SEQ ID NO: 24)

An analogous procedure to that described in Example 2.6 was used, except that the whole of the peptide assembly was performed manually using HBTU/DIPEA activation, coupling Fmoc-Papa-OH, Fmoc-Ala-OH, Fmoc-Arg(Pbf)-OH, Fmoc-IIb-OH and 5-phenylvaleric acid in the appropriate order. The peptide was cleaved from the resin using a similar procedure to that described in Example 2.6. The product was purified using preparative RP-HPLC in a similar manner to that described for Example 1.4, eluting with a gradient of acetonitrile-water containing 0.1% TFA (15–30% acetonitrile) over 90 minutes at a flow rate of 10 ml/minute. The product was characterised by HPLC, mass spectroscopy and amino acid analysis in a similar manner to that described for Example 1.4; RP-HPLC (eluting with acetonitrile and water containing 0.1% TFA, using a 15–30% acetonitrile gradient over 30 minutes, flow rate 1.0 ml/minute) retention time=20.02 minutes; mass spectrometry, m/e (ES+) 1061.6 (MH$^+$), 531.4 (M+2H$^{++}$); amino acid analysis gave Ala 4.16, Arg 2.00, IIb present.

EXAMPLE 24

3-(2-Cyanobenzoibithiophen-5-yl)propionyl-Ala-Arg-Ala-IIb-Ala-Arg-Ala-Papa-NH$_2$ (SEQ ID NO: 25)

The synthesis and purification was performed manually using similar methodology to that described for Example 1.4, coupling and deprotecting the Fmoc-Papa-OH (used instead of Fmoc-Pip-OH), Fmoc-protected amino acids and Fmoc-IIb-OH in the appropriate order, and using 3-(2-cyanobenzo[b]thiophen-5-yl)propionic acid instead of 5-phenylvaleric acid. The product was purified using preparative RP-HPLC in a similar manner to that described for Example 1.4, eluting with a gradient of acetonitrile-water containing 0.1% TFA (15–40% acetonitrile) over 60 minutes at a flow rate of 10 ml/minute. The product was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.0 ml/minute) retention time=17.58 minutes; mass spectrometry, m/e (ES+) 1114.7 (MH$^+$); amino acid analysis gave Arg 2.86, Ala 4.12, IIb 1.00.

3-(2-Cyanobenzo[b]thiophen-5-yl)propionic acid was obtained as follows:

(a) Raney Nickel (1 g) and hydrazine hydrate (3 ml) was added to ethyl 5-nitrobenzo[b]thiophene-2-carboxylate (25 g) (obtained as described in Syn. Comm., (1991), 21, 959–964) in ethanol (500 ml) at 60° C. A vigorous reaction ensued and the mixture refluxed. Further portions of Raney Nickel (1 g) and hydrazine hydrate (3 ml) were added at 10 minute intervals until a total of 15 ml had been added and the mixture was then refluxed for 90 minutes. The hot mixture was filtered and the filtrate evaporated. The residue was dissolved in hot ethanol (300 ml) and activated charcoal was added. The mixture was filtered and the filtrate evaporated to dryness to give ethyl 5-aminobenzo[b]thiophene-2-carboxylate (18 g) as a pale yellow solid. The solid was added to a stirred mixture of concentrated hydrochloric acid (50 ml) and water (130 ml) at −0C. A solution of sodium nitrite (5.6 g) in water (20 ml) was added slowly and then the mixture was allowed to stir at 0° C. for a further 30 minutes. A solution of potassium iodide (130 g) in water (200 ml) was then added. The mixture was allowed to warm to ambient temperature and then heated at 50° C. for 30 minutes. The mixture was allowed to cool, extracted with chloroform (150 ml) and the organic layer washed with sodium metabisulphite solution. The organic phase was dried (MgSO$_4$) and evaporated to give a brown oil. The oil was purified by chromatography on silica using a gradient of hexane increasing to 10% ethyl acetate/hexane. The appropriate fractions were combined and evaporated to give ethyl 5-iodobenzo[b]thiophene-2-carboxylate (14 g) as an oil; NMR (d$_6$-DMSO): 1.35 (t, 3H), 4.4 (q, 2H), 7.8 (dd, 1H), 7.9 (d, 1H), 8.15 (s, 1H), 8.45 (d, 1H).

(b) Sodium hydroxide (5 g) in water (150 ml) was added to ethyl 5-iodobenzo[b]thiophene-2-carboxylate (14 g) in ethanol (200 ml) and the mixture was stirred for 16 hours. The mixture was concentrated to about 150 ml by evaporation and the mixture was adjusted to ~pH 3 by addition of dilute hydrochloric acid. The mixture was then extracted with diethyl ether (2×100 ml). The combined organic extracts were dried (MgSO$_4$) and evaporated to give 5-iodobenzo[b]thiophene-2-carboxylic acid (11.7 g) as a solid; NMR (d$_6$-DMSO): 7.8 (dd, 1H), 7.9 (d, 1H), 8.05 (s, 1H), 8.45 (d, 1H).

(c) Oxalyl chloride (2.7 ml) and DMF (1 drop) was added to 5-iodobenzo[b]thiophene-2-carboxylic acid (3.05 g) in dichloromethane (30 ml), whereupon evolution of gas began. After gas evolution had ceased, the mixture was evaporated to dryness and the residue was dissolved in THF (10 ml). The solution was added to concentrated aqueous ammonia (25 ml) in portions. After the addition was complete, the mixture was stirred for 1 hour. The solid which precipitated was collected by filtration, washed with water and dried under vacuum. The solid (3 g) was dissolved in DMF (15 ml) and the mixture was added at 0° C. to a mixture of DMF(20 ml) and phosphoryl chloride (3 g). The mixture was stirred for 2 hours. The mixture was then added to water (60 ml) and the solid which precipitated was collected by filtration, washed with water and dried under vacuum to give 2-cyano-5-iodobenzo[b]thiophene (2.65 g) as a pale yellow powder; NMR (d$_6$-DMSO): 7.9 (dd, 1H), 8.0 (d, 1H), 8.3 (s, 1H), 8.45 (d, 1H).

(d) Methyl acrylate (2 g), triethylamine (2.35 g) and palladium acetate (0.05 g) was added to 2-cyano-5-iodobenzo[b]thiophene (4.8 g) in DMF (25 ml) and the mixture was stirred under argon at 90° C. for 30 minutes. The mixture was allowed to cool and then added to water (50 ml). The solid which precipitated was collected by filtration and dissolved in chloroform. Activated charcoal was added and the mixture filtered and the filtrate dried (MgSO$_4$). Solvent was removed by evaporation to give methyl3-(2-cyanobenzo[b]thiophen-5-yl)acrylate (2.5 g); NMR (d$_6$-DMSO): 3.75 (s, 3H), 6.7 (d, 1H), 7.8 (d, 1H), 8.0 (dd, 1H), 8.2 (d, 1H), 8.3 (d, 1H), 8.85 (s, 1H).

(e) Methyl 3-(2-cyanobenzo[b]thiophen-5-yl)acrylate (2.5 g) was hydrogenated in THF (20 ml) using 10% palladium on carbon (0.5 g) as catalyst until the majority of the starting material had disappeared by thin layer chromatography (silica plates eluting with ethyl acetate/hexane 1:4). The mixture was filtered and evaporated to give methyl 2-cyanobenzo[b]thiophene-5-propionate (1.45 g) contaminated with ~20% of starting material. Sodium hydroxide (0.23 g) was added to a mixture of this product (1.4 g) in THF (10 ml) and uater (3 ml) and the mixture was stirred for 2 hours. The mixture was adjusted to ~pH 5 with concentrated hydrochloric acid and concentrated by evaporation to remove the THF present.

The pH of the mixture was then adjusted to ~pH 3 with concentrated hydrochloric acid and the mixture extracted with dichloromethane. The extract was dried (MgSO$_4$) and evaporated. The residue was purified by reverse phase chromatography using C$_{18}$ support and a gradient of 40% methanol/water increasing to 75% methanol/water. The appropriate fractions were combined and evaporated to give 2-cyanobenzo[b]thiophene-5-propionic acid (0.28 g) as a white solid.; NMR (CDCl$_3$): 2.88 (t, 2H), 3.1 (t, 2H), 7.4 (d, 1H), 7.75 (s, 1H), 7.8 (d, 1H), 7.85 (s, 1H).

EXAMPLE 25

Phv-Arg-Ala-Ala-IIb-Ala-Arg-Ala-Papa-NH$_2$ (SEQ ID NO: 26)

The synthesis was performed manually, and the purification carried out, using similar methodology to that described for Example 1.4, coupling and deprotecting the Fmoc-Papa-OH (used instead of Fmoc-Pip-OH), Fmoc-protected amino acids and Fmoc-IIb-OH in the appropriate order. The product was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.0 ml/minute) retention time= 17.45 minutes; mass spectrometry, m/e (ES$^+$) 1061.9 (MH$^+$); amino acid analysis gave Arg 1.94, Ala 4.04, IIb 1.02.

EXAMPLE 26

Phv-Arg-Ile-Ala-IIb-Ala-Arg-Ala-Papa-NH$_2$ (SEQ ID NO: 27)

The synthesis was performed automatically on an automatic synthesiser (ABI 431) using similar methodology to that described in Example 2.6, coupling the Fmoc-Papa-OH and Fmoc-protected amino acids in the appropriate order, with the exception that the Fmoc-IIb-OH was incorporated manually. The product was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.0 ml/minute) retention time=20.7 minutes; mass spectrometry, m/e (ES$^+$) 1103.8 (MH$^+$); amino acid analysis gave Arg 1.92, Ala 3.03, IIb 0.96, Ile 1.08.

EXAMPLE 27

Phv-Ile-Arg-Ala-IIb-Leu-Arg-Ala-Papa-NH$_2$ (SEQ ID NO: 28)

The synthesis was performed manually, and the purification carried out, using similar methodology to that described for Example 1.4, coupling and deprotecting the Fmoc-Papa-OH (used instead of Fmoc-PipOH), Fmoc-protected amino acids and Fmoc-IIb-OH in the appropriate order. The product was characterised by HPLC, mass spectroscopy and amino acid analysis in a similar manner to that described for Example 1.4; RP-HPLC (eluting with acetonitrile and water containing 0.1% TFA, using a 10–50% acetonitrile gradient over 30 minutes, flow rate 1.0 ml/minute) retention time=23.8 minutes; mass spectrometry, m/e (ES$^+$) 1145.7 (MH$^+$); amino acid analysis gave Arg 1.98, Ala 1.92, Leu 0.99, Ile 1.09, IIb present.

EXAMPLE 28

Phv-Ala-Arg-Ala-IIc-Ala-Ala-Ala-Papa-NH$_2$ (SEQ ID NO: 29)

The synthesis was performed manually, using similar methodology to that described for Example 1.4, coupling and deprotecting the Fmoc-Papa-OH (used instead of Fmoc-Pip-OH), Fmoc-protected amino acids and Fmoc-IIc-OH in the appropriate order. The product did not require purification by preparative HPLC. The product was characterised by HPLC, mass spectroscopy and amino acid analysis in a similar manner to that described for Example 1.4; RP-HPLC (eluting with acetonitrile and water containing 0.1% TFA, using a 20–40% acetonitrile gradient over 20 minutes, flow rate 1.0 ml/minute) retention time=10.45 minutes; mass spectrometry, m/e (ES$^+$) 962.5 (MH$^+$), 492.8 (M+H+Na)$^{++}$; amino acid analysis gave Ala 4.90, Arg 1.00. IIc present.

Fmoc-IIc-OH was obtained using an analogous procedure to that described in Example 1 for the preparation of Fmoc-IIb-OH but using glycine methyl ester hydrochloride in place of L-alanine methyl ester hydrochloride in step 1.1. The following intermediates were obtained:

Boc-(D)-Met-Gly-OMe; in 80% yield; NMR (CDCl$_3$): 1.4d (s, 9H), 2.0d (m, 1H), 2.1d (m, 1H), 2.1d (s, 3H), 2.6d (t, 2H), 3.8d (s, 3H), 4.05d (m, 2H), 4.4d (m, 1H), 5.3d (bs, 1H), 6.8d (bs, 1H);

Methyl 2-[(3R -3-(N-[tert-butyloxycarbonyl]amino)-2-oxo-pyrrolidin-1-yl]acetate; in 50% yield; NMR (CDCl$_3$): 1.45d (s, 9H), 2.0d (m, 1H), 2.6d (m, 1H), 3.4d (m, 2H), 3.8d (s, 3H), 4.05d (q, 2H), 4.1d (m, 1H). 5.55 (bs, 1H);

2-[(3R)-3(N-[9-fluorenylmethyloxycarbonyl]amino)-2-oxo-pyrrolidin-1-yl]acetic acid; in 75% yield; NMR (d$_6$-DMSO): 1.9d (m, 1H), 2.3d (m, 1H), 3.3d (m, 2H), 4.0d (q, 2H), 4.3d (m, 4H), 7.4d (m, 4H), 7.6d (m, 2H), 7.9d (d, 2H).

EXAMPLE 29

Phv-Arg-Ala-Ala-IIb-Ala-Ala-Ala-Papa-NH$_2$ (SEQ ID NO: 30)

The synthesis was carried out automatically on an ACT 357 automated peptide synthesiser (using Rink Amide MBHA resin), coupling the Fmoc-Papa-OH and Fmoc-protected amino acids in the appropriate order, with the exception that the the Fmoc-IIb-OH was incorporated manually. The automatic couplings were performed, following the manufacturer's recommended conditions for single acylations, by activation of the carboxylic acid (1 mmol) with diisopropylcarbodiimide (1 equivalent) and HOBT (1 equivalent) in DMF for approximately 11 minutes before transfer to the resin. The acylation was carried out for approximately 60 minutes and the washing and deprotection procedures carried out in a similar manner to that described in Example 2.6. The manual coupling of the Fmoc-IIb-OH was carried out in a Bond Elut tube using HBTU/HOBT chemistry. The 5-phenylvaleric acid required a double couple to obtain a positive result by the Kaiser test. The peptide was then cleaved from the resin and purified by preparative RP-HPLC using similar methodology to that described in Example 1.4. The product was characterised by HPLC, mass spectroscopy and amino acid analysis in a similar matter to that described for Example 1.4; RP-HPLC (eluting with acetonitrile and water containing 0.1% TFA, using a 20–35% acetonitrile gradient over 15 minutes, flow rate 1.0 ml/minute) retention time=10.33 minutes; mass spectroscopy, m/e (ES$^+$) 976.5 (MH$^+$), 499.9 (M+H+Na)$^{++}$; amino acid analysis gave Ala 5.02, Arg 1.00, IIb 1.22.

EXAMPLE 30

Phv-Lys(=C(NMe$_2$)$_2$)-Ala-Ala-Ala-Thr-IIb-Ala-Papa-NH$_2$ (SEQ ID NO: 31)

Using an analogous procedure to that described in Example 15(a), but using Fmoc-Lys(Boc)-OH in place of Fmoc-Dap(Boc)-OH, there was thus obtained, after the peptide was cleaved from the resin and purification by preparative RP-HPLC, Phv-Lys-Ala-Ala-Ala-Thr-IIb-Ala-Papa-NH$_2$ (SEQ ID NO:62) (270 mg). The peptide (270 mg) was then stirred in a mixture of HBTU (94 mg), diisopropylethylamine (88 microliters) and DMF (50 ml) for 16 hours. The mixture was evaporated and the residue purified by preparative RP-HPLC using a analogous procedure to that described in Example 15(a). The peptide was characterised by HPLC, mass spectroscopy and amino acid analysis in a similar manner to that described in Example 1.4; RP-HPLC (10–40% acetonitrile gradient over 40 minutes, flow rate 1.2 ml/minute) retention time=29.83 minutes; mass spectroscopy, m/e (ES$^+$) 1077.27 (MH$^+$): amino acid analysis gave Thr 1.0, Ala 4.3. Arg 1.00. IIb present; tetramethylhomoarginine present.

EXAMPLES 31–33

Phv-Arg-Ala-Ala-Ala-Thr-IIb-Ala-Papa-NHCH$_2$CH$_2$-Morpholine (Example 31) (SEQ ID NO: 32)

Phv-Arg-Ala-Ala-Ala-Thr-IIb-Ala-Papa-OCH$_3$ (Example 32) (SEQ ID NO: 33)

Phv-Arg-Ala-Ala-Ala-Thr-IIb-Ala-Papa-OH (Example 33) (SEQ ID NO: 34)

Hydroxymethyl polystyrene resin (1.67 g, 1 mmol) was stirred at ambient temperature with Fmoc-Papa-OH (1.5 g, 4 mmol), diisopropylcarbodiimide (0.628 ml, 4 mmol) and dimethylaminopyridine (61 mg, 0.5 mmol) in DMF (5 ml) and dichloromethane (20 ml) for 2 hours. The resin was filtered and washed with DMF (5×20 ml) and methanol (5×20 ml) and dried in vacuo at 40° (yield 2.105 g). The peptide resin was then transferred to an automated synthesiser (ABI 430A) and the remaining Fmoc-protected amino acids coupled in a manner similar to that described in Example 2.6, to give the protected peptide resin (2.992 g). The peptide resin was then suspended in a mixture of DMF (10 ml) and methanol (10 ml) and 4-(2-aminoethyl) morpholine (0.88 ml), was added followed by a catalytic amount of potassium cyanide (50 mg). After 7 days at ambient temperature, the mixture was filtered and the resin was washed with DMF (5×20 ml). The resin was immediately re-suspended in a mixture of DMF (10 ml), methanol (10 ml) and potassium cyanide (50 mg). After 4 days, the mixture was filtered and the resin was washed with DMF (5×20 ml). All of the filtrates and washings from both treatments were combined and evaporated to dryness. After deprotection with 90% TFA/H$_2$O and removal of volatile material by evaporation, the residue was purified by preparative RP-HPLC, using a similar procedure to that described in Example 1.4, to give 3 products. The products were characterised as follows:

Phv-Arg-Ala-Ala-Ala-Thr-IIb-Ala-Papa-NHCH$_2$CH$_2$-Morpholine (SEQ ID NO: 32) (40 mg);
RP-HPLC (10–50% acetonitrile gradient over 40 min, flow rate 1.2 ml/minute) retention time=19.5 minutes; mass spectrometry, m/e (ES+) 1119.8 (MH)+; amino acid analysis gave Thr 0.58, Ala 3.84, Arg 1.16, IIb 1.00;
Phv-Arg-Ala-Ala-Ala-Thr-IIb-Ala-Papa-OMe (SEQ ID NO: 33) (37 mg);
RP-HPLC (10–50% acetonitrile gradient over 40 min, flow rate 1.2 ml/minute) retention time=27.7 minutes; mass spectrometry, m/e (ES$^+$) 1021.6 (MH)$^+$; amino acid analysis gave Thr 0.61, Ala 3.80, Arg 1.22, IIb 0.97;
Phv-Arg-Ala-Ala-Ala-Thr-IIb-Ala-Papa-OH (SEQ ID NO: 34) (155 mg);

RP-HPLC (10–50% acetonitrile gradient over 40 min, flow rate 1.2 ml/minute) retention time=24.2 minutes; mass spectrometry, m/e (ES+) 1007.5 (MH)$^+$; amino acid analysis gave Thr 0.62, Ala 3.78, Arg 1.20, IIb 0.98.

EXAMPLE 34

Phv-Arg-Ala-Ala-Ala-Thr-IIb-Ala-Papa-N(CH$_2$CH$_2$)$_2$N—(CH$_2$)$_2$O(CH$_2$)$_2$OH (SEQ ID NO: 35)

4-[2-(2-hydroxyethoxy)ethyl]piperazine (235 mg) was added to a mixture of Phv-Arg-Ala-Ala-Ala-Thr-IIb-Ala-Papa-OH (SEQ ID NO:34) (135 mg), HBTU (51 mg), DIPEA (47 microliters) and DMF (10 ml) and the mixture was stirred for 60 minutes. Volatile material was removed by evaporation, and the residue was purified by preparative HPLC, using a similar procedure to the described in Example 1.4, to give Phv-Arg-Ala-Ala-Ala-Thr-IIb-Ala-Papa-N(CH$_2$CH$_2$)$_2$NCH$_2$CH$_2$-OCH$_2$CH$_2$OH (SEQ ID NO: 35) (115 mg). The peptide was characterised by HPLC, mass spectrometry and amino acid analysis in a similar manner to that described for Example 1.4; RP-HPLC (eluting with acetonitrile and water containing 0.1% TFA, using a 10–50% acetonitrile gradient over 40 minutes, flow rate 1.2 ml/minute) retention time=18.83 minutes; mass spectrometry, m/e (ES+) 1163.8 (MH)$^+$; amino acid analysis gave Thr 0.62, Ala 3.80, Arg 1.22, IIb 0.97.

EXAMPLE 35

The compounds of the invention may be administered for therapeutic or prophylactic use to warm-blooded animals such as man in the form of conventional pharmaceutical compositions, a typical example of which includes the following:

Injectable Solution 0.01 to 100 mg of active ingredient is dissolved in up to 2 ml of an aqueous injection vehicle to give a concentration of active ingredient between 0.01 to 100 mg/ml. The aqueous injection vehicle is buffered to a pH between 5 and 8 using a pharmaceutically acceptable buffer (for example, phosphate, or acetate) and contains a pharmaceutically acceptable tonicity adjustment agent (for example, sodium chloride or dextrose) added to achieve isotonicity. The vehicle may optionally also contain other pharmaceutically acceptable excipients such as solubilising agents (for example, DMSO, ethanol, propylene glycol or polyethylene glycol) preservatives and antioxidants. The active ingredient may typically be an Example described hereinbefore and may conveniently be present as a pharmaceutically acceptable salt.

Chemical Formulae

P—R$^1$—R$^2$—R$^3$—R$^4$     I

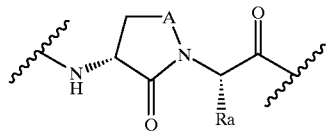

II

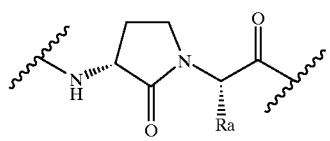

IIa

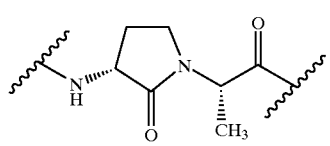

IIb

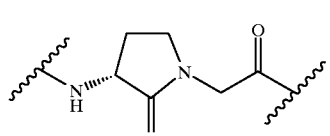

IIc

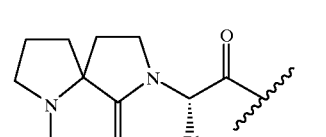

III

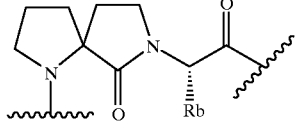

IIIa

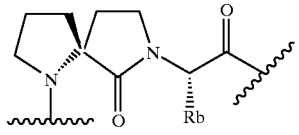

IIIb

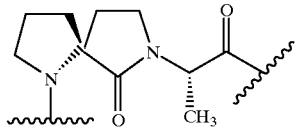

---

What we claim is:

1. A peptide derivative of the formula I, P—$R^1$—$R^2$—$R^3$—$R^4$, or a pharmaceutically acceptable salt thereof, wherein P is a hydrophobic residue;

$R^1$ is a sequence of 5 L-amino acids and $R^3$ is a single L-amino acid; or $R^1$ is a sequence of 3 L-amino acids and $R^3$ is a sequence of 3 L-amino acids;

$R^2$ is a group of formula II or formula III

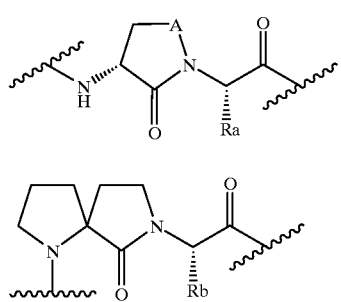

in which Ra and Rb are independently selected from hydrogen and (1–4C)alkyl and A is methylene or oxygen; and $R^4$ is OH, $NH_2$ or NRcRd wherein Rc is selected from (1–4C)alkyl, 2-carbamoylcyclopentyl, 2-pyridylmethyl, 4-carbamoylcyclohexyl, 4-carbamoylcyclohexylmethyl, 3-carbamoylphenyl, 4-carbamoylphenyl, 4-(carbamoylmethyl)phenyl, 4-(carboxymethyl)phenyl, 4-(methoxycarbonylmethyl)-phenyl, 2-morpholinoethyl and a group of the formula —$A^1$—$G^1$ in which $A^1$ is (3–7C)alkylene or $A^1$ is selected from (1) a group of the formula —$A^2$—$B^2$— in which $A^2$ is p-phenylene or 1,4-cyclohexylene and $B^2$ is (1–4C)alkylene or $A^2$ is methylene and $B^2$ is p-phenylene or 1,4-cyclohexylene; and (2) a group of the formula —$A^3$—$B^3$—$C^3$3- in which $A^3$ is methylene, $B^3$ is p-phenylene or 1,4-cyclohexylene and $C^3$ is (1–3C)alkylene; and $G^1$ is a group of the formula —N=C[N(Rp)$_2$]$_2$ in which each Rp is independently selected from hydrogen, methyl, ethyl and propyl; or $A^1$ is a group of the formula —$A^4$—$B^4$— in which $A^4$ is p-phenylene and $B^4$ is —$CH_2$—CO— and $G^1$ is 2-morpholinoethyl or 4-[2-(2-hydroxyethoxy)ethyl]piperazin-1-yl;

and Rd is hydrogen or (1–4C)alkyl; or $R^4$ is 1-piperazinyl, 4-methyl-1-piperazinyl, 4-amidino-1-piperazinyl, 4-(2-(2-hydroxyethoxy)ethyl)-1-piperazinyl, 1-piperidyl or 4-substituted-1-piperidyl wherein the 4-substitutent is selected from carboxy, carbamoyl, N-(2-aminoethyl)carbamoyl and N-(4-aminobutyl)carbamoyl; or R⁴ is a sequence of 1 to 6 amino acids or an amide thereof.

2. A peptide derivative, or pharmaceutically acceptable salt thereof as claimed in claim 1 in which P is an aliphatic, aromatic or mixed aliphatic/aromatic organic group of from 5 to 20 carbon atoms, or a heteroaromatic or mixed aliphatic/heteroaromatic organic group of from 5 to 20 carbon atoms and 1.2 or 3 heteroatoms selected from oxygen, sulphur and nitrogen.

3. A peptide derivative, or a pharmaceutically acceptable salt thereof, as claimed in claim 1 in which R⁴ is OH, NH₂ or NRcRd wherein Rc is selected from (1–4C)alkyl, 2-carbamoylcyclopentyl, 2-pyridylmethyl, 4-carbamoylcyclohexyl, 4-carbamoylcyclohexylmethyl, 3-carbamoylphenyl, 4-carbamoylphenyl, 4-(carbamoylmethyl)phenyl, 4-(carboxymethyl)phenyl, 2-morpholinoethyl and a group of the formula —A¹—G¹ in which A¹ is (3–7C)alkylene or A¹ is selected from
- (1) a group of the formula —A²—B²— in which A² is p-phenylene or 1,4-cyclohexylene and B² is (1–4C) alkylene or A² is methylene and B² is p-phenylene or 1,4-cyclohexylene; and
- (2) a group of the formula —A³—B³—C³— in which A³ is methylene, B³ is p-phenylene or 1,4-cyclohexylene and C³ is (1–3C)alkylene; and G¹ is a group of the formula —N═C[N(Rp)₂]₂ in which each Rp is independently selected from hydrogen, methyl, ethyl and propyl; and Rd is hydrogen or (1–4C)alkyl; or R⁴ is 1-piperazinyl, 4-methyl-1-piperazinyl, 4-amidino-1-piperazinyl, 4-(2-(2-hydroxyethoxy)ethyl)-1-piperazinyl, 1-piperidyl or 4-substituted-1-piperidyl wherein the 4-substitutent is selected from carboxy, carbamoyl, N-(2-aminoethyl)carbamoyl and N-(4-aminobutyl)carbamoyl; or R⁴ is a sequence of 1 to 6 amino acids or an amide thereof.

4. A peptide derivative, or pharmaceutically acceptable salt thereof, as claimed in claim 1 or 2 in which P is an aliphatic, aromatic or mixed aliphatic/aromatic organic group of from 5 to 20 carbon atoms;
the L-amino acids comprising R¹ and R³ are independently selected from Ala, Glu, Gly, His, Ile, Lys, Asn, Gln, Arg, Thr and Val;
and R⁴ is OH, NH₂, NHRc wherein Rc is selected from (1–4C)alkyl, 2-carbamoylcyclopentyl, 2-pyridyimethyl, 4-carbamoylcyclohexyl, 4-carbamoylcyclohexylmethyl, 3-carbamoylphenyl, 4-carbamoylphenyl and 4-(carbamoylmethyl)phenyl; or R⁴ is 1-piperazinyl, 4-methyl-1-piperazinyl, 4-amidino-1-piperazinyl, 1-piperidyl or 4-substituted-1-piperidyl wherein the 4-substitutent is selected from carboxy, carbamoyl, N-(2-aminoethyl)carbamoyl and N-(4-aminobutyl)carbamoyl; or R⁴ is a sequence of 1 to 6 amino acids or an amide thereof.

5. A peptide derivative, or pharmaceutically acceptable salt thereof, as claimed in claim 1 or 2 wherein R¹ is a sequence of 5 L-amino acids represented as AA1—AA2-AA3-AA4-AA5 in which AA1 is selected from Ala, Ile, Tyr, Val, Glu, Lys, Arg, Gly, Gap, GapMe₄ and 3,3,3-trifluoroalanine;

AA2 is selected from Ala, Lys, Glu, Sar, Val, Arg, Gly, Pro, Ile, Tic, 3,3,3-trifluoroalanine and N⁶-diethylLys;

AA3 is selected from Ala, His, Gln, Val, Thr, Glu, Gly, Asp, Asn and N³-diethylDap;

AA4 is selected from Ala, Lys, Asn, Arg, Thr, Glu, Sar, Gly, Pro, His and N⁶-diethylLys; and AA5 is selected from Thr, Val, Ala, Gly, Dap, Dab, Pro, Hyp, Asn and N³-diethylDap; and R³ is a single amino acid selected from Ala, Gly, Dap, azaalanine and azaglycine.

6. A peptide derivative, or a pharmaceutically acceptable salt thereof, as claimed in claim 1 or 2 wherein R¹ is a sequence of 3 L-amino acids represented as AA1-AA2-AA3 in which AA1 is selected from Ala, Ile, Tyr, Val, Glu, Lys, Arg, Gly, Gap, GapMe₄ and 3,3,3-trifluoroalanine;

AA2 is selected from Ala, Lys, Glu, Sar, Val, Arg, Gly, Pro, Ile, Tic, 3,3,3-trifluoroalanine and N⁶-diethylLys; and AA3 is selected from Ala, His, Gln, Val, Thr, Glu, Gly, Asp, Asn and N³-diethylDap;

and R³ is selected from a sequence of 3 L-amino acids represented as AA6-AA7-AA8 in which AA6 is selected from Gly, Leu, Lys, Ala, Pro, Glu, Sar, His and Dap;

AA7 is selected from Pro, Ala, Lys, Arg, Glu, Sar, Gly, Oic and Dic; and

AA8 is selected from from Ala, Gly, Dap, azaalanine and azaglycine.

7. A peptide derivative, or pharmaceutically acceptable salt thereof, as claimed in claim 1 or 2 wherein R² is a group of the formula IIb

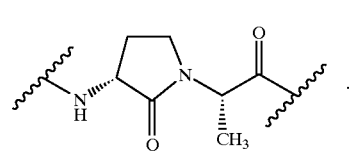

IIb

8. A peptide derivative, or a pharmaceutically acceptable salt thereof, as claimed in claim 1 or 2 wherein hydrophobic group P is 5-phenylvaleryl.

9. A peptide derivative, or a pharmaceutically acceptable salt thereof, as claimed in claim 1 or 2 wherein R⁴ is 4-carbamoyl-1-piperidyl, 4-(carbamoylmethyl)anilino or 4-(2-guanidinoethyl)anilino.

10. A peptide derivative as claimed in claim 1, or a pharmaceutically acceptable salt thereof, which is selected from (SEQ ID NO: 5)

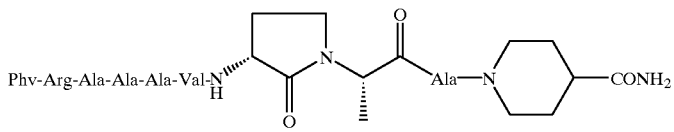

(SEQ ID NO: 17)

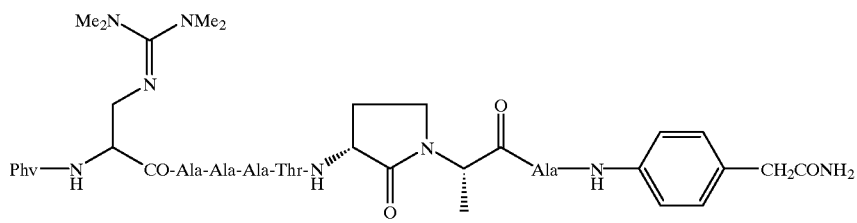

(SEQ ID NO: 20)

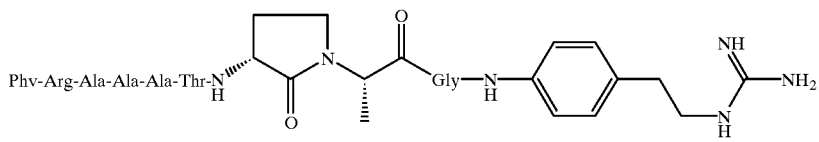

(SEQ ID NO: 24)

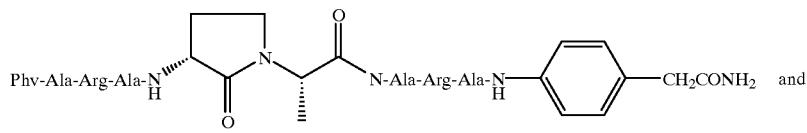

and

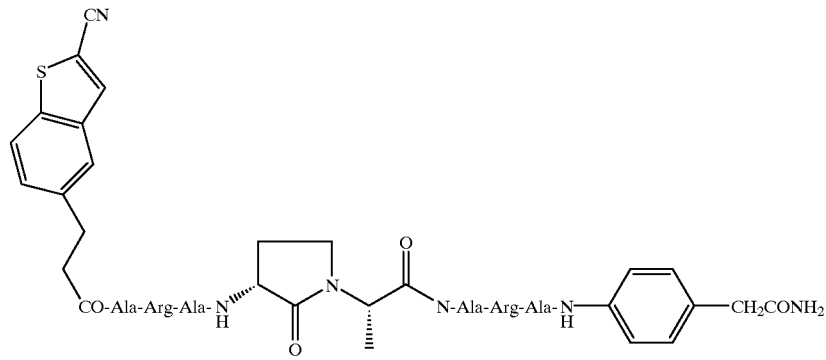

or a pharmaceutically acceptable salt thereof, in which Phv represents a 5-phenylvaleryl group.

11. A pharmaceutical composition which comprises a peptide derivative as claimed in claim 1, or a pharmaceutically acceptable salt thereof, in association with a pharmaceutically acceptable diluent or carrer.

12. A process for the manufacture of a peptide derivative, or a pharmaceutically acceptable salt thereof, as claimed in claim 1, comprising sequentially coupling in the appropriate order suitably protected amino acids or sequences of two or more suitably protected amino acids, a suitably protected group of the formula H—II—OH or H—III—OH and optionally a suitably protected group of the formula $R^4$—H, followed by optional functional group modification of the N-terminal amino group, to introduce a hydrophobic group P and removal of any remaining protecting groups and any solid support.

13. A method for treating a MHC class II dependent T-cell mediated autoimmune or inflammatory disease which comprises administering to a warm-blooded mammal in need of such treatment an effective amount of a peptide derivative as claimed in claim 1, or a pharmaceutically acceptable salt thereof.

14. A method as claimed in claim 13 for treating rheumatoid arthritis or multiple sclerosis.

15. A peptide derivative having the formula

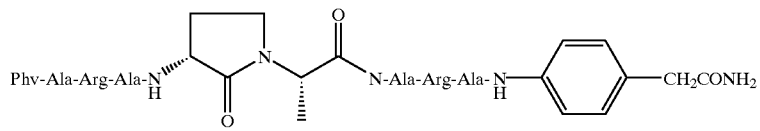

or a pharmaceutically acceptable salt thereof.

* * * * *

UNITED STATES PATENT AND TRADEMARK OFFICE
CERTIFICATE OF CORRECTION

PATENT NO. : 6,087,336
DATED : July 11, 2000
INVENTOR(S) : Edwards et al.

It is certified that error appears in the above-identified patent and that said Letters Patent is hereby corrected as shown below:

Column 9,
The formulas for SEQ ID NO: 24 and SEQ ID NO: 25 should read as follows:

(SEQ ID NO: 24)

and

Example 23

(SEQ ID NO: 25)

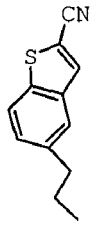

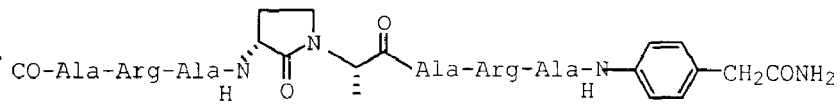

Example 24

Columns 85 and 86,
SEQ ID NO: 24 should read as follows:

(SEQ ID NO: 24)

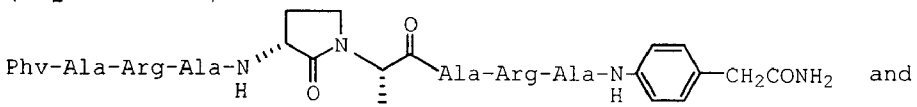 and

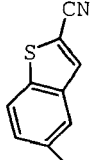

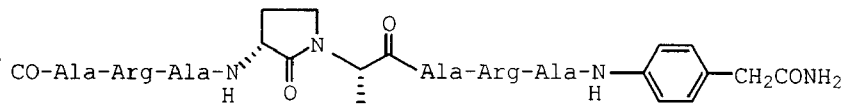

UNITED STATES PATENT AND TRADEMARK OFFICE
CERTIFICATE OF CORRECTION

PATENT NO. : 6,087,336
DATED : July 11, 2000
INVENTOR(S) : Edwards et al.

It is certified that error appears in the above-identified patent and that said Letters Patent is hereby corrected as shown below:

Column 88,
Claim 15 should read as follows:

15. A peptide derivative having the formula or a pharmaceutically acceptable salt thereof.

Signed and Sealed this

Twenty-sixth Day of August, 2003

JAMES E. ROGAN
*Director of the United States Patent and Trademark Office*